(12) United States Patent
Matsumoto et al.

(10) Patent No.: US 7,465,747 B2
(45) Date of Patent: Dec. 16, 2008

(54) FLUORESCENT LABEL COMPOUNDS

(75) Inventors: Kazuko Matsumoto, 3-9-12-105, Daizawa, Setagaya-ku, Tokyo 155-0032 (JP); Jingli Yuan, Liaoning Province (CN); Guilan Wang, Liaoning Province (CN); Mingqian Tan, Liaoning Province (CN)

(73) Assignees: Kazuko Matsumoto, Tokyo (JP); Tokyo Chemical Industry Co., Ltd., Tokyo (JP)

( * ) Notice: Subject to any disclaimer, the term of this patent is extended or adjusted under 35 U.S.C. 154(b) by 612 days.

(21) Appl. No.: 10/506,242

(22) PCT Filed: Mar. 10, 2003

(86) PCT No.: PCT/JP03/02774

§ 371 (c)(1),
(2), (4) Date: May 25, 2005

(87) PCT Pub. No.: WO03/076938

PCT Pub. Date: Sep. 18, 2003

(65) Prior Publication Data

US 2005/0255465 A1    Nov. 17, 2005

(30) Foreign Application Priority Data

Mar. 8, 2002 (JP) ............................. 2002-063961
Sep. 18, 2002 (JP) ............................. 2002-271924

(51) Int. Cl.
C07D 401/02 (2006.01)
A61K 31/44 (2006.01)

(52) U.S. Cl. ........................... 514/334; 514/183; 540/1; 546/257

(58) Field of Classification Search .................... None
See application file for complete search history.

(56) References Cited

FOREIGN PATENT DOCUMENTS

| | | | |
|---|---|---|---|
| CN | 1407052 A | 4/2003 |
| EP | 1 491 629 A1 | 12/2004 |
| JP | 1-503806 | 12/1989 |
| JP | 3-500297 | 1/1991 |
| JP | 7-506667 | 7/1995 |
| JP | 2001-335574 | 12/2001 |
| WO | WO 93/11433 | 6/1993 |
| WO | WO 03/076615 A1 | 9/2003 |

OTHER PUBLICATIONS

U.S. Appl. No. 10/506,242, filed Sep. 8, 2004, Matsumoto, et al.
U.S. Appl. No. 10/506,240, filed Sep. 8, 2004, Matsumoto, et al.
Jingli Yuan, et al., "Synthesis of a Terbium Fluorescent Chelate and its Application to Time-Resolved Fluoroimmunoassay", Analytical Chemistry, vol. 73, No. 8, XP-001030284, Apr. 15, 2001, pp. 1869-1876.
Veli-Matti Mukkala, et al., "Development of luminescent europium (III) and Terbium (III) chelats of 2,2':6',2"-terpyridine derivatives for protein labelling", Helvetica Chimica Acta, vol. 76, pp. 1361-1378 1993.

*Primary Examiner*—Zinna N Davis
(74) *Attorney, Agent, or Firm*—Oblon, Spivak, McClelland, Maier & Neustadt, P.C.

(57) ABSTRACT

It is intended to provide novel labeling reagents characterized by having a group capable of binding to a substance to be labeled (for example, a biological substance, a physiologically active substance, etc.), easily forming a complex together with a rare earth ion, the complex being stable in an aqueous solution, and having a sufficient fluorescence intensity and a long fluorescence life time regardless of buffer types; complexes composed of the above labeling reagent with a rare earth ion; fluorescence labels containing the above complex; a fluorescence assay method using the above fluorescent label; etc. Namely, labeling reagents comprising a compound having a 2,2':6',2"-tripyridine skeleton or a 2,6-dipyrazolopyridine skeleton and having a group capable of binding to a substance to be labeled (for example, a biological substance, a physiologically active substance, etc.) and a group capable of forming a complex together with a rare earth ion; complexes composed of the above labeling reagent with a rare earth ion; fluorescence labels containing the above complex; a fluorescence labeling method using the above complex as a label; and a fluorescence assay method using the above fluorescent label.

29 Claims, 6 Drawing Sheets

FLUORESCENT LABEL COMPOUNDS

This application is a 371 of PCT/JP03/02774 filed Mar. 10, 2003.

TECHNICAL FIELD

The present invention relates to a novel labeling reagent, a complex comprising the labeling reagent and a rare earth metal ion, a fluorescent labeling agent comprising the complex, a fluorescent labeling method using the complex as a labeling agent, a fluorescence assay method using the fluorescent labeling agent and a reagent for a fluorescence assay method.

BACKGROUND ART

Conventionally, as an analysis method for a trace amount of a substance in a biological specimen, an immunoassay with the use of an antibody-antigen reaction, a DNA hybridization assay or the like has been commonly used. In these analysis methods, a labeling agent for labeling an antibody, an antigen, a DNA, a DNA base derivative, a DNA oligonucleotide or the like needs to be used. As a labeling agent enabling a highly sensitive detection, labeling with a fluorescence, labeling with a radioactive isotope, labeling with an enzyme or the like is commonly used.

Labeling with a radioactive isotope is highly sensitive, however, it has a drawback in that it involves a risk when the radioactive isotope is stored, used and disposed. In addition, labeling with an enzyme has problems in that the molecular weight of an enzyme is high, an enzyme is susceptible to the external environment such as temperature, therefore it is unstable, and its reproducibility is low, and has a drawback in that by binding an enzyme labeling agent to a substance to be labeled, the activities of the enzyme and the labeled substance are decreased.

In addition, as a labeling method with a fluorescence, labeling with an organic fluorescent dye (for example, fluorescein, rhodamine, dansyl chloride or the like) is known. However, it has a drawback in that fluorescence detection of an organic fluorescent dye is disturbed to a large extent by the background noise due to the scattering light of the excitation light or the background noise derived from the fluorescence of other coexisting substances in a sample, whereby it becomes difficult to perform a highly sensitive assay.

As a labeling method with a fluorescence other than this, labeling with a rare earth fluorescent complex is known. A rare earth fluorescent complex has fluorescence characteristics of a long fluorescence lifetime (a rare earth fluorescent complex has a fluorescence lifetime of several ten or several hundred microseconds or more compared with a fluorescence lifetime of several nanoseconds of a common fluorescent substance), a large Stokes shift and a sharp fluorescence peak. By using these characteristics, a time-resolved fluorescence assay method using a rare earth fluorescent complex as a labeling agent has been already developed. Due to these characteristics, by using a time-resolved fluorescence assay, the interference by the background fluorescence with a short lifetime derived from an excitation light or a biological sample can be removed, thereby enabling a highly sensitive assay.

As one of the time-resolved fluorescence assay systems with the use of a rare earth complex as a labeling agent, there is the "DELFIA" (Dissociation-Enhanced Lanthanide Fluoroimmunoassay) developed by PerkinElmer Life Sciences, Inc. (previously, Wallac). This system is a method of performing a fluorescence assay by labeling a protein, a nucleic acid or the like with the use of, as a labeling agent, a complex of isothiocyanatophenyl-EDTA or isothiocyanatophenyl-DTTA (DTTA=diethylenetriamine tetraacetate) with a rare earth ion, adding so-called a fluorescence enhancement solution containing β-diketone-trioctylphosphineoxide (TOPO) and Triton X-100 before measuring fluorescence, releasing a rare earth metal ion from a nonfluorescent complex, and forming a micelle solution of a ternary complex of β-diketone, a rare earth ion and TOPO (E. Soini, T. Lovgren, CRC Crit. Rev. Anal. Chem., 1987, 18, 105-154; E. P. Diamandis, T. K. Christopoulos, Anal. Chem., 1990, 62, 1149A-1157A; I. Hemmila, J. Alloys Compd., 1995, 225, 480-485). However, in this DELFIA system, excess β-diketone and TOPO are present in the measured solution, and if they react with a rare earth metal ion from the environment, they can emit strong fluorescence. Therefore, the system has a major drawback in that it is very susceptible to the contamination of rare earth metal ions. Furthermore, the DELFIA system has drawbacks in that a fluorescence enhancement solution needs to be added, there are lots of measurement steps, and that a solid-phase assay cannot be performed.

As another time-resolved fluorescence assay system with the use of a rare earth complex as a labeling agent, there is the FIAgen system developed by Diamandis et al. in Canada (E. P. Diamandis, Clin. Biochem., 1988, 21, 139-150; E. F. G. Dickson, A. Pollak, E. P. Diamandis, Pharmac. Ther., 1995, 66, 207-235). The FIAgen system is an assay method using a fluorescent europium complex (4,7-bis(chlorosulfophenyl)-1,10-phenanthroline-2,9-dicarboxylate(BCPDA)-$Eu^{3+}$), which can directly label a protein. In this system, there is not a problem of the contamination of europium from the environment, and a solid-phase assay can be performed. However, the fluorescence intensity of the labeling agent in this system is weaker than that in the above-mentioned DELFIA system by at least two orders of magnitude. Therefore, the system has drawbacks in that the detection sensitivity is low, and that a highly sensitive analysis is difficult.

As the other time-resolved fluorescence assay systems with the use of a rare-earth-complex as a labeling agent, there is the TRACE (time resolved amplified cryptate emission) assay system of CIS Bio International in France (G. Mathis, Clin. Chem., 1995, 41, 1391-1397; G. Mathis, J. Clin. Ligand Assay, 1997, 20, 141-147). This system has an advantage in that after reaction in a homogenized solution was finished, a time-resolved fluorescence assay can be continuously performed with the use of a europium fluorescent labeling agent, tris(bipyridine)cryptate-$Eu^{3+}$, and an organic fluorescent labeling agent, allophycocyanin, as a donor for fluorescence energy transfer and a receptor, and has merits in that a solid phase material is not used and B/F separation or washing operation is not required. However, it has a disadvantage in that the sensitivity is low, therefore, the system cannot be applied to a highly sensitive assay.

To overcome the above-mentioned drawbacks of the time-resolved fluorescence assay method with the use of a rare earth fluorescent complex labeling agent and the systems, the present inventors have already developed chlorosulfonyl quadridentate β-diketone labeling agents that can directly label a protein having an amino group and have investigated an application to a time-resolved fluorescence assay method using these (JP-A-9-241233; JP-A-2000-111480; J. Yuan, G. Wang, K. Majima, K. Matsumoto, Anal. Chem., 2001, 73, 1869-1876; S. Sueda, J. Yuan, K. Matsumoto, Bioconjugate Chem., 2000, 11, 827-831; K. Matsumoto, J. Yuan, G. Wang, H. Kimura, Anal. Biochem., 1999, 276, 81-87; J. Yuan. K.

Matsumoto, H. Kimura, Anal. Chem., 1998, 70, 596-601; J. Yuan, G. Wang, K. Matsumoto, H. Kimura, Anal. Biochem., 1997, 254, 283-287).

However, the above-mentioned chlorosulfonyl quadridentate β-diketone labeling agents generally have poor solubility in water. Therefore, it has a drawback in that if it labeled a small biological substance (for example, a nucleic acid base with a low molecular weight having an amino group, or other organic compounds), the solubility of the labeled biological substance is decreased, whereby the substance precipitates from the solution. Also, its chelating ability is not sufficient, therefore, it has a drawback in that the buffer types that can be used are restricted. Accordingly, an application to direct labeling of these substances involves difficulties.

As the information of the prior art documents associated with the invention of this application, there are as follows:

1. JP-A-9-241233
2. JP-A-2000-111480
3. E. Soini, T. Lovgren, CRC Crit. Rev. Anal. Chem., 1987, 18, 105-154;
4. E. P. Diamandis, T. K. Christopoulos, Anal. Chem., 1990, 62, 1149A-1157A
5. I. Hemmila, J. Alloys Compd., 1995, 225, 480-485
6. E. F. G. Dickson, A. Pollak, E. P. Diamandis, Pharmac. Ther., 1995, 66, 207-235
7. E. P. Diamandis, Clin. Biochem., 1988, 21, 139-150
8. G. Mathis, Clin. Chem., 1995, 41, 1391-1397
9. G. Mathis, J. Clin. Ligand Assay, 1997, 20, 141-147
10. J. Yuan, G. Wang, K. Majima, K. Matsumoto, Anal. Chem., 2001, 73, 1869-1876;
11. S. Sueda, J. Yuan, K. Matsumoto, Bioconjugate Chem., 2000, 11, 827-831;
12. K. Matsumoto, J. Yuan, G. Wang, H. Kimura, Anal. Biochem., 1999, 276, 81-87;
13. J. Yuan. K. Matsumoto, H. Kimura, Anal. Chem., 1998, 70, 596-601;
14. J. Yuan, G. Wang, K. Matsumoto, H. Kimura, Anal. Biochem., 1997, 254, 283-287

DISCLOSURE OF THE INVENTION

The present invention has been conducted considering the above-mentioned circumstances, and makes it an object to provide a novel labeling reagent characterized in that it has a binding group capable of binding to a substance to be labeled (for example, a biological substance, a physiologically active substance or the like) and easily forms a complex together with a rare earth ion, and furthermore, the complex is stable sufficiently in an aqueous solution and has a sufficient fluorescence intensity and a long fluorescence lifetime regardless of the types of buffer, and a complex comprising the labeling reagent and a rare earth metal ion, a fluorescent labeling agent comprising the complex, a fluorescence assay method using the fluorescent labeling agent and the like.

BEST MODE FOR CARRYING OUT THE INVENTION

Figure 1:
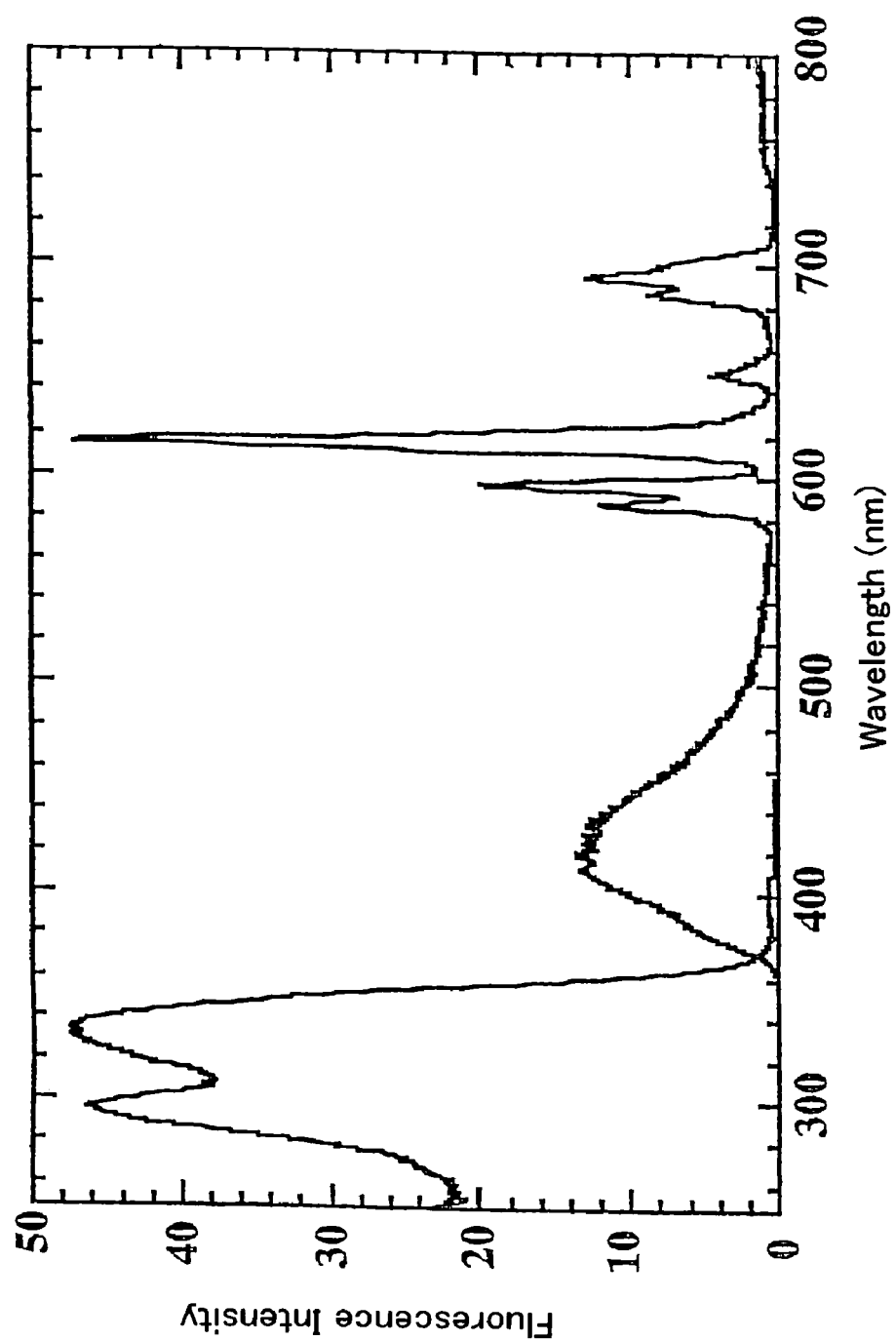
FIG. 1 is a diagram showing the fluorescence spectra of the solution of ATTTA-Eu$^{3+}$ of the present invention. [ATTTA-Eu$^{3+}$]=1.0×10$^{-6}$ M in 0.05 M borate buffer solution (pH 9.1).

The present invention relates to a labeling reagent comprising a compound having a 2,2':6',2''-tripyridine skeleton or a 2,6-dipyrazolopyridine skeleton and having a binding group capable of binding to a substance to be labeled and a binding group capable of forming a complex together with a rare earth ion, more particularly to a fluorescent labeling reagent.

Also, the present invention relates to a complex comprising the above-mentioned labeling reagent and a rare earth metal ion, a fluorescent labeling agent comprising the complex, and a fluorescent labeling method characterized by using the complex as a labeling agent.

Furthermore, the present invention relates to a biological substance or a physiologically active substance labeled with the above-mentioned fluorescent labeling agent.

Still furthermore, the present invention relates to a fluorescence assay method characterized by using the complex as a fluorescent labeling agent, a reagent for a fluorescence assay method comprising the complex as a fluorescent labeling agent and a reagent kit comprising the complex as a fluorescent labeling agent.

Also, the present invention relates to a fluorescent labeling method characterized by using the above-mentioned labeling reagent and a rare earth metal ion.

Furthermore, the present invention relates to a biological substance or a physiologically active substance being fluorescently labeled with the above-mentioned labeling reagent and a rare earth metal ion.

Still furthermore, the present invention relates to a fluorescence assay method characterized by using the above-mentioned labeling reagent and a rare earth metal ion, a reagent for a fluorescence assay method comprising the above-mentioned labeling reagent and a rare earth metal ion, and a reagent kit comprising the above-mentioned labeling reagent and a rare earth metal ion.

Also, the present invention relates to a compound represented by the general formula [1]:

[1]

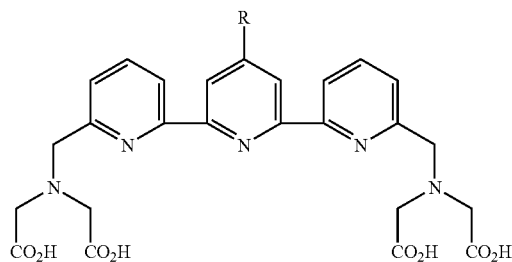

(wherein R represents an aryl group, an aryl group having an active substituent, a heterocyclic group or a heterocyclic group having an active substituent) or its salt.

Furthermore, the present invention relates to a compound represented by the general formula [2]:

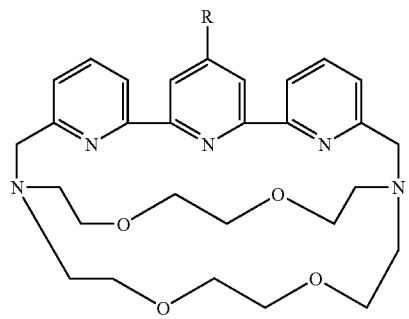

[2]

(wherein R represents an aryl group, an aryl group having an active substituent, a heterocyclic group or a heterocyclic group having an active substituent) or its salt.

Still furthermore, the present invention relates to a compound represented by the general formula [3]:

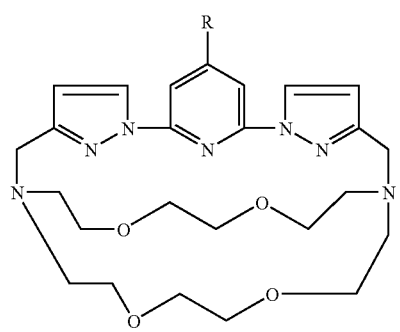

[3]

(wherein R represents an aryl group, an aryl group having an active substituent, a heterocyclic group or a heterocyclic group having an active substituent) or its salt.

Also, the present invention relates to a compound represented by the general formula [4]:

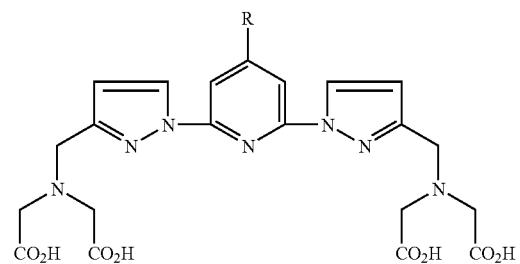

[4]

(wherein R represents an aryl group, an aryl group having an active substituent, a heterocyclic group or a heterocyclic group having an active substituent) or its salt.

Namely, the present inventors have intensively studied in order to solve the above-mentioned problems. As a result, they have found that a compound having a 2,2':6',2''-tripyridine skeleton or a 2,6-dipyrazolopyridine skeleton in the organic ligand molecule, and also having-many carboxylic acid groups or crown ether groups is easily soluble in water, and capable of easily forming a stable fluorescent complex together with a rare earth ion, and also found that by introducing an active substituent capable of easily binding to a substance to be labeled (labeled substance) into the same organic ligand molecule, a biological molecule such as a protein can be labeled under a mild condition, thus the present invention has been completed.

The active substituent capable of binding to a substance to be labeled (labeled substance) is a group that can react with a specific substituent, which these labeled substances have, and can form a covalent binding group.

Also, the novel labeling reagent according to the present invention is easily soluble in water, therefore, even though a labeled substance is a small molecule, it will have a sufficient solubility in water even after it is labeled.

Specific examples of the compound having a 2,2':6',2''-tripyridine skeleton or a 2,6-dipyrazolopyridine skeleton and having a binding group capable of binding to a substance to be labeled and a binding group capable of forming a complex together with a rare earth ion include, for example, a compound represented by the following general formula [1]:

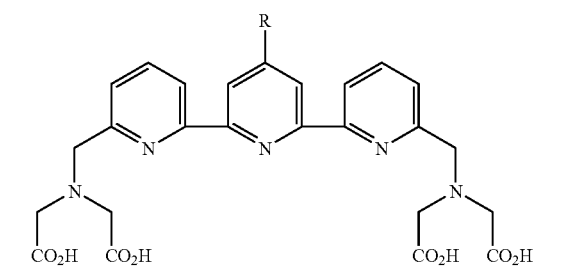

[1]

(wherein R represents an aryl group, an aryl group having an active substituent, a heterocyclic group or a heterocyclic group having an active substituent) or its salt, a compound represented by the following general formula [2]:

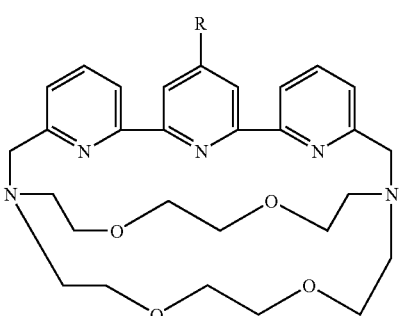

[2]

(wherein R represents an aryl group, an aryl group having an active substituent, a heterocyclic group or a heterocyclic group having an active substituent) or its salt, a compound represented by the following general formula [3]:

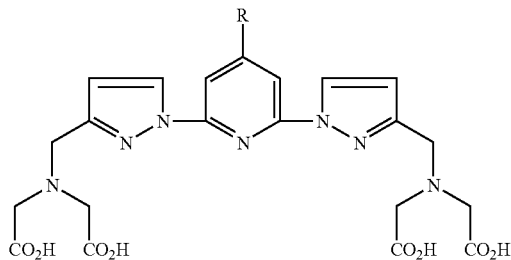

[3]

(wherein R represents an aryl group, an aryl group having an active substituent, a heterocyclic group or a heterocyclic group having an active substituent) or its salt, a compound represented by the following general formula [4]:

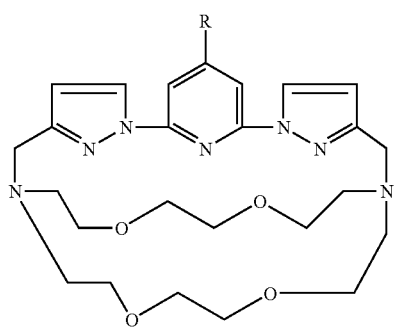

[4]

(wherein R represents an aryl group, an aryl group having an active substituent, a heterocyclic group or a heterocyclic group having an active substituent) or its salt and the like.

Any of the compounds represented by the above-mentioned general formulae [1] to [4] is a novel compound.

In the above-mentioned general formulae [1] to [4], examples of the aryl group or the aryl group for an aryl group having an active substituent represented by R include a monocyclic, polycyclic, or condensed ring aromatic hydrocarbon group having 6 to 30 carbons, preferably 6 to 20 carbons, more preferably 6 to 14 carbons, more specifically they include, for example, a phenyl group, a tolyl group, a xylyl group, a naphthyl group, a methylnaphthyl group, an anthryl group, a phenanthryl group, a 2-biphenyl group, a 3-biphenyl group, a 4-biphenyl group and the like.

Also, examples of the heterocyclic group or the heterocyclic group for a heterocyclic group having an active substituent include a saturated or unsaturated monocyclic, polycyclic, or condensed ring heterocyclic group having at least one nitrogen atom, oxygen atom or sulfur atom in the ring, in which one ring is a 5 to 20-membered ring, preferably 5 to 10-membered ring, more preferably 5 to 7-membered ring, and which may be condensed with a carbocyclic group such as a cycloalkyl group, a cycloalkenyl group or an aryl group, more specifically they include; for example, a pyridyl group, a thienyl group, a phenylthienyl group, a thiazolyl group, a furyl group, a piperidyl group, a piperazyl group, a pyrrolyl group, a morpholino group, an imidazolyl group, an indolyl group, a quinolyl group, a pyrimidinyl group and the like.

The active substituent of an aryl group or a heterocyclic group may be any substituent as long as it is an active substituent capable of binding to a substance to be labeled (labeled substance), which can react with a specific substituent that these labeled substances have, and can form a covalent binding group. However, preferred examples include an amino group, an isothiocyanate group, a halogenoacetylamino group, a hydrazino group, a (4,6-dihalogeno-1,3,5-triazene-2-yl)amino group, a carboxyl group and the like.

Here, examples of the halogeno group in the halogenoacetylamino group or the (4,6-dihalogeno-1,3,5-triazene-2-yl)amino group include —Cl, —Br, —I and the like.

Preferred examples of the R group in the above-mentioned general formulae [1] to [4] include a phenyl group, a 4-aminophenyl group, a 2-pyridyl group, a 6-amino-2-pyridyl group, a 2-thienyl group, a 5-amino-2-thienyl group, a 4-biphenyl group, a 4'-amino-4-biphenyl group and the like.

With respect to the salts of the compounds represented by the above-mentioned general formulae [1] to [4], examples for an acid group such as a carboxyl group include a salt of an alkali metal such as sodium or potassium and examples for a basic group such as an amino group include a salt of an acid such as hydrochloric acid or sulfuric acid.

There is no restriction on the structure of the complex comprising a labeling reagent comprising the compound according to the present invention and a rare earth metal ion as mentioned above. It is easy to select the type of the rare earth ion by considering the fluorescence intensity, fluorescence wavelength, fluorescence lifetime and the like of the complex to be formed. A complex with a trivalent lanthanoid ion is preferable, in particular, a complex with a trivalent europium ion, a trivalent terbium ion, a trivalent samarium ion or a trivalent dysprosium ion is preferable.

The complex formed by complexation of a rare earth metal ion with the labeling reagent according to the present invention is a fluorescent complex, therefore, the complex according to the present invention can be used as a fluorescent labeling agent.

The fluorescent labeling agent according to the present invention is an agent comprising the complex according to the present invention, however, the fluorescent labeling agent according to the present invention includes any of what has been isolated as a complex, a solution comprising the complex, a solution comprising a rare earth metal ion and the labeling reagent according to the present invention.

The fluorescent labeling-method according to the present invention is performed by fluorescently labeling various substances to be labeled with the use of a complex comprising the labeling reagent according to the present invention and a rare earth metal ion as a labeling agent, in other words, with the use of the above-mentioned fluorescent labeling agent according to the present invention, or with the use of the above-mentioned labeling reagent according to the present invention and a rare earth metal ion.

In the case where a labeling reagent and a rare earth metal ion are used, there are (1) a method of fluorescently labeling a substance by first reacting a substance to be labeled with a labeling reagent, then making an appropriate rare earth metal ion work thereby forming a complex, and (2) a method of performing a complex formation and fluorescent labeling in parallel by reacting a labeling reagent, a rare earth metal ion and a substance to be labeled at the same time, and it is arbitrary which method is used.

There is no particular restriction on the labeled substance to be labeled by the labeling reagent or the fluorescent labeling agent according to the present invention, and it can widely be applied to a biological substance, a physiologically active substance, other chemical substances and the like. In addition, the labeled substance is not limited by the molecular size thereof, the existing form (solution or solid phase) thereof, or whether it is a single or composite substance, or the like. The proviso of the labeled substance to be labeled by the fluorescent labeling agent according to the present invention is that at least one reaction group capable of covalently binding to the fluorescent labeling agent according to the present invention may exist in part of the labeled substance, or such a group may be able to be introduced.

Examples of such a biological substance or a physiologically active substance capable of being labeled by the fluorescent labeling agent according to the present invention include, for example, an enzyme, a protein, a peptide (oligopeptide or polypeptide), a sugar, a glycoprotein, a hormone, a lipid, a nucleic acid, a nucleic acid derivative, a nucleic acid probe, an oligonucleotide, a cell, a fatty compound, an amino acid, a medicinal substance (including an antibiotic) and the like.

Also, specific examples of the protein include an antibody and its derivative, an antigen and its derivative, an avidin (including streptavidin), a serum albumin, various haptens, a hormone, protein A, protein G and the like.

Examples of other chemical substances include an agricultural chemical, an ordinary chemical product, a chemical reagent, an industrial chemical product and the like.

The fluorescence assay method according to the present invention is characterized in that an assay is performed with the use of as a fluorescent labeling agent, a complex comprising the labeling reagent according to the present invention and a rare earth metal ion, or an assay is performed by fluorescently labeling various substances to be labeled with the use of the labeling reagent according to the present invention and a rare earth metal ion.

Typical examples of the fluorescence assay method include, for example, a time-resolved fluorescence assay method.

Application examples of the time-resolved fluorescence assay method include, for example, a time-resolved fluoroimmunoassay method, a DNA hybridization assay method, a chromatography method, a fluorescence microscopy method and the like.

The reagent for a fluorescence assay method according to the present invention is a reagent used for the fluorescence assay method according to the present invention and is characterized by comprising, as a fluorescent labeling agent, a complex comprising the labeling reagent according to the present invention and a rare earth metal ion or comprising the labeling reagent according to the present invention and a rare earth metal ion.

The reagent for a fluorescence assay method according to the present invention can be used for an assay of a biological substance, a physiologically active substance, other chemical substances or the like. In particular, it is more effective for an assay of a biological substance or a physiologically active substance.

Specific examples of the biological substance or the physiologically active substance are as described above.

The reagent kit according to the present invention is a reagent kit used for the fluorescence assay method according to the present invention, and comprises, as a fluorescent labeling agent, a complex comprising the labeling reagent according to the present invention and a rare earth metal ion or comprises the labeling reagent according to the present invention and a rare earth metal ion.

There is no particular restriction on a synthetic method, a starting material or the like of the labeling reagent according to the present invention, and any labeling reagent can be synthesized by combining a common organic synthetic method as needed. The structural identification of a product may be performed by using a common structural analysis method for an organic chemical, such as $^1$H NMR or an organic elementary analysis method.

The synthetic method of the labeling reagent represented by the general formula [1] according to the present invention is shown by the following reaction scheme taking the case where R is a 5-amino-2-thienyl group as an example.

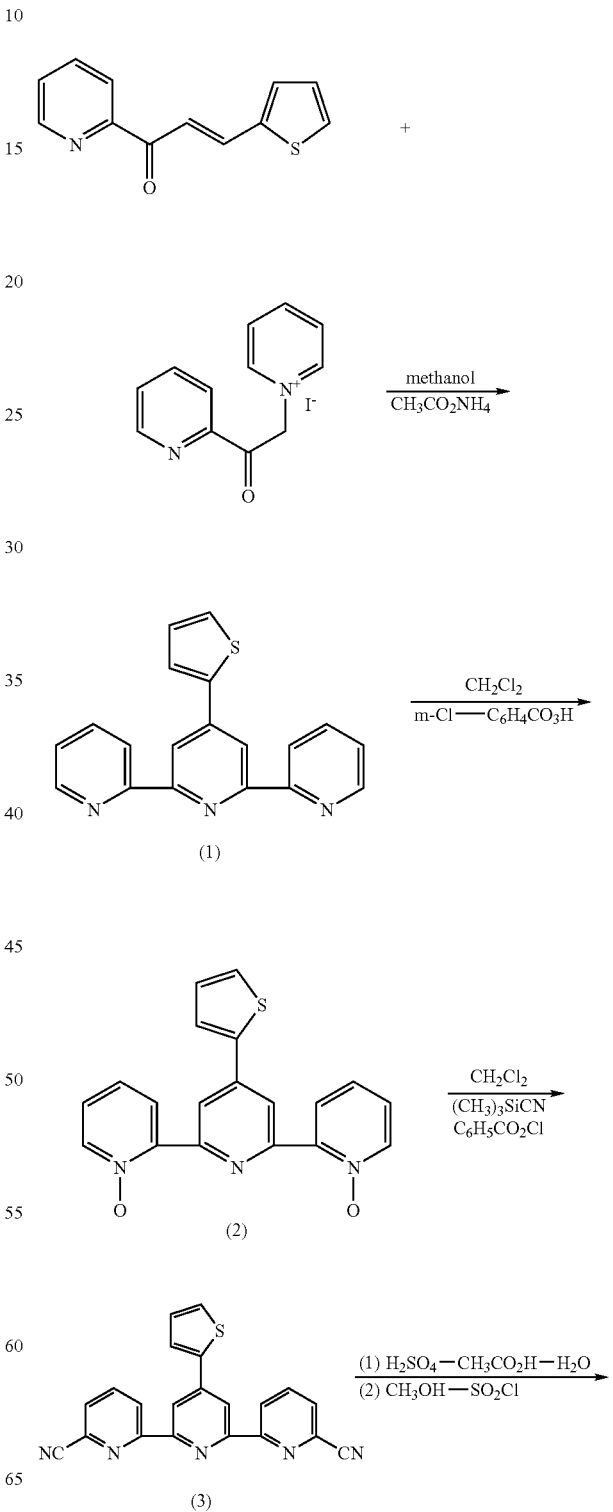

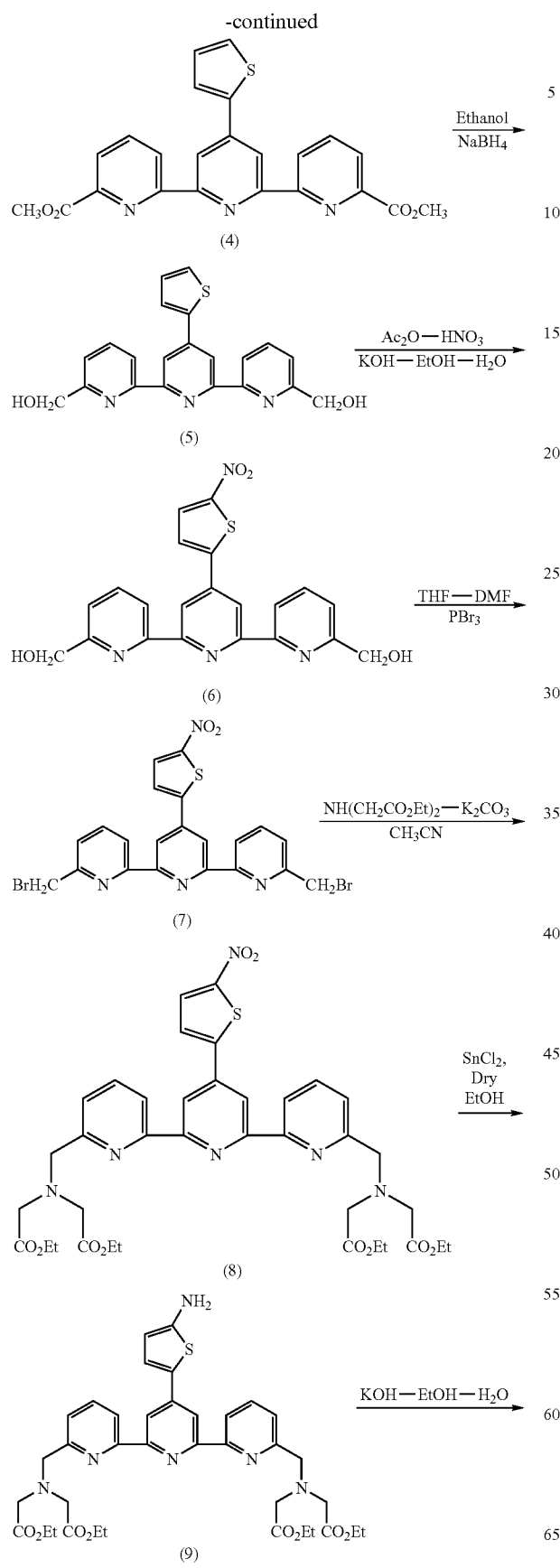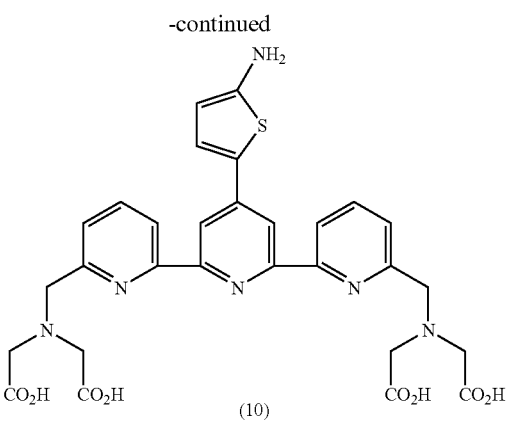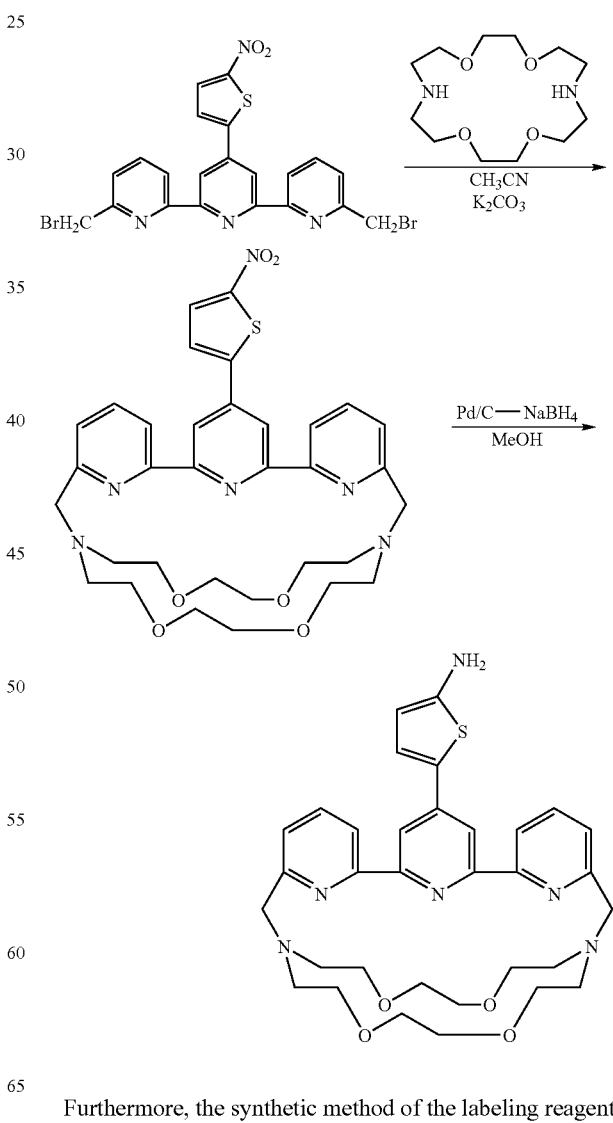
Also, the synthetic method of the labeling reagent represented by the general formula [2] according to the present invention is shown by the following reaction scheme taking the case where R is a 5-amino-2-thienyl group as an example.
Furthermore, the synthetic method of the labeling reagent represented by the general formula [3] according to the present invention is shown by the following reaction scheme taking the case where R is a 5-amino-2-thienyl group as an example.

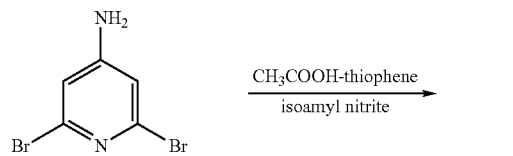

(11)

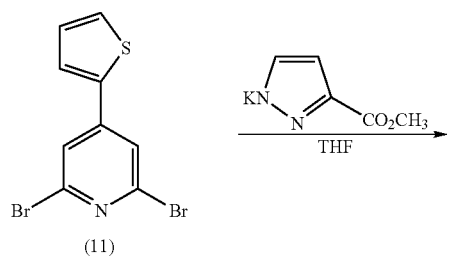

(12)

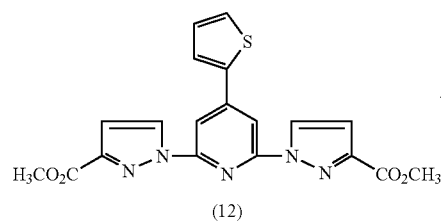

(13)

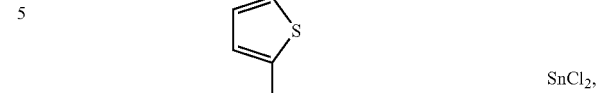

(16)

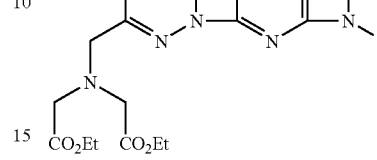

(17)

(14)

(15)

(18)

Still furthermore, the synthetic method of the labeling reagent represented by the general formula [4] according to the present invention is shown by the following reaction scheme taking the case where R is a 5-amino-2-thienyl group as an example.

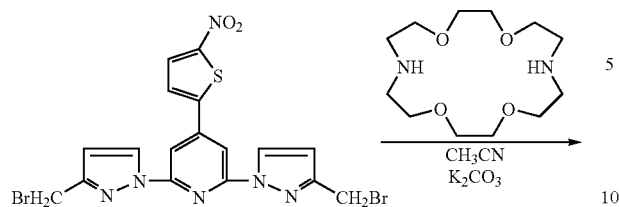

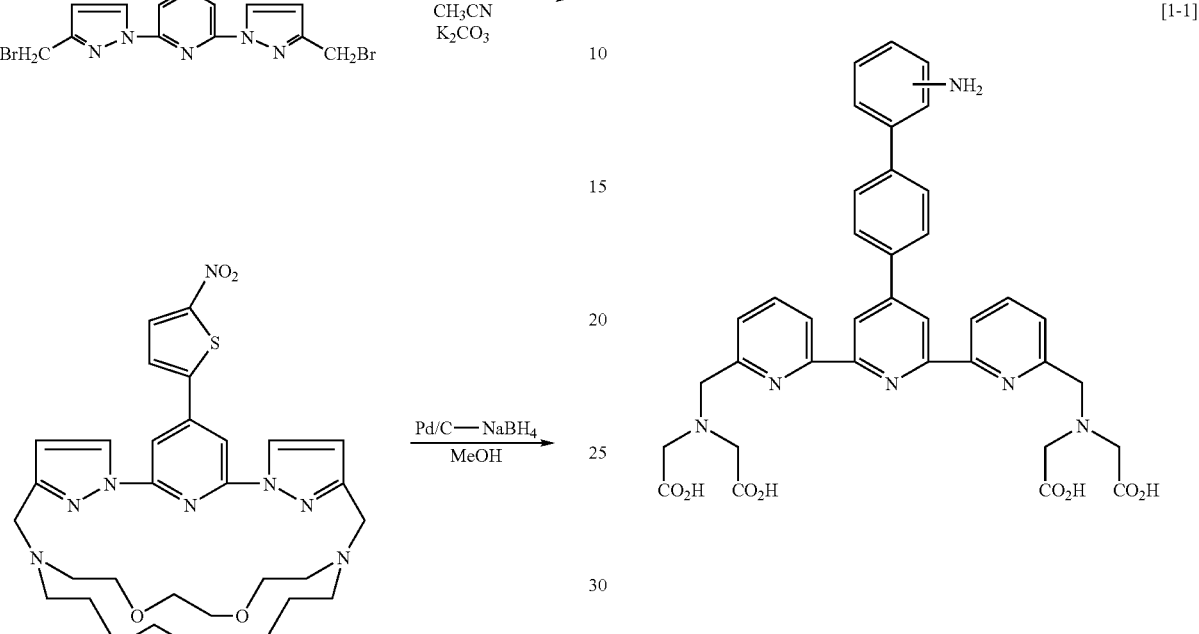

Preferred examples of the compounds represented by the general formulae [1] to [4] and the salt thereof according to the present invention include other than the above-mentioned compound whose R group is a 5-amino-2-thienyl group, a compound whose R group is a 4-biphenyl group and a compound whose R group is a 4'-amino-4-biphenyl group. More specific examples of the compound whose R group is a 4-biphenyl group and a compound whose R group is a 4'-amino-4-biphenyl group can include the compound represented by the following general formula [1-1],

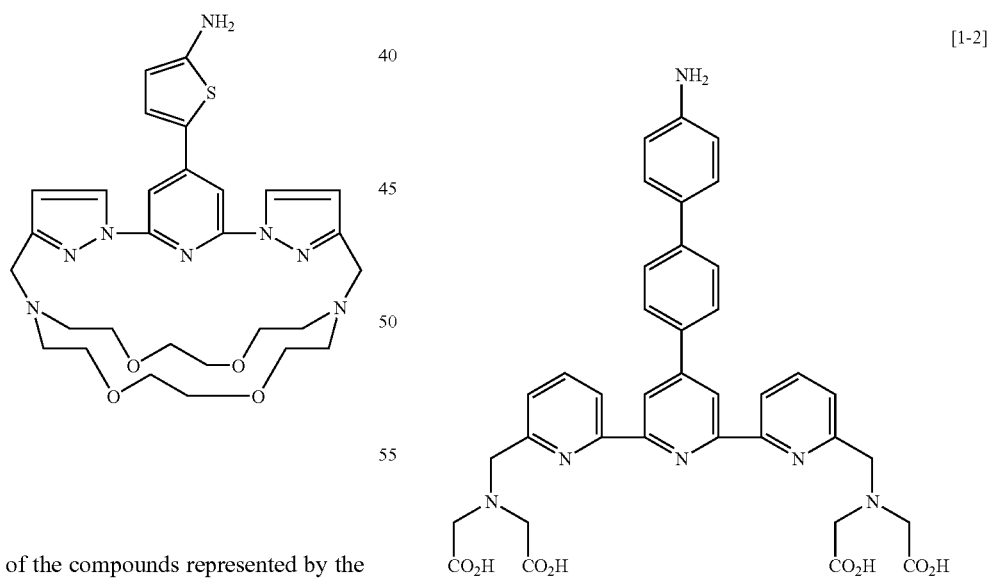

[1-1]

further specific examples can include the compound represented by the following general formula [1-2],

[1-2]

the compound represented by the following general formula [2-1]:

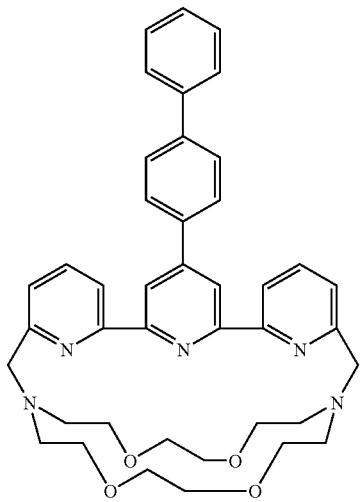

[2-1]

and the like.

Incidentally, all the content described in the specifications JP-A-2002-063961 and JP-A-2002-271924 is incorporated in this description.

EXAMPLES

Hereunder, the present invention will be explained in more detail with reference to Examples, however the present invention is not limited to these Examples.

Example 1

Synthesis of N,N,N',N'-[(4'-(5'''-amino-2'''-thienyl)-2,2':6',2''-terpyridine-6,6''-diyl)bis(methylenenitrilo)] tetrakis(acetate) (abbreviated as ATTTA)

(1) Synthesis of 4'-(2'''-thienyl)-2,2':6',2''-terpyridine [Compound (1)]

N-[2-(pyrido-2'-yl)-2-oxoethyl]pyridinium iodide (16.3 g, 50 mmol), (E)-3-(2''-thienyl)-1-(pyrido-2'-yl)-2-propenone (10.76 g, 50 mmol) and ammonium acetate (23.1 g) were added to 500 ml of dried methanol, then the solution was refluxed for 24 hours while stirring. The reaction solution was cooled and a precipitate was obtained by filtration. After the precipitate was washed thoroughly with chilled methanol, recrystallized from acetonitrile, thus the compound (1) was obtained. The yield after vacuum drying was 43.8%. The product was confirmed to be the target compound by $^1$H NMR.

1H NMR (CDCl$_3$): δ8.74 (d, J=7.9 Hz, 2H), 8.69 (s, 2H), 8.64 (d, J=7.9 Hz, 2H), 7.87 (t, J=7.9 Hz, 2H), 7.78 (d, J=3.6 Hz, 1H), 7.44 (d, J=5.1 Hz, 1H), 7.38-7.32 (m, 1H).

(2) Synthesis of 4'-(2'''-thienyl)-2,2':6',2''-terpyridine-1,1''-dioxide [Compound (2)]

After the compound 1 (12.6 g, 40 mmol) was dissolved in 500 ml of CH$_2$Cl$_2$, 40 g of 3-chloroperoxybenzoic acid was added and stirred for 20 hours at room temperature. The reaction solution was washed with 10% Na$_2$CO$_3$ aqueous solution (4×200 ml), and the organic layer was dried with Na$_2$SO$_4$, then, the solvent was removed under reduced pressure. The product was dissolved in 300 ml of methanol, and a trace amount of insoluble substances was removed by filtration, then the solvent was removed under reduced pressure. The product was washed well with acetonitrile and vacuum dried, thus the compound (2) was obtained. The yield was 61.4%. The product was confirmed to be the target compound by $^1$H NMR.

$^1$H NMR (CDCl$_3$): δ 9.23 (s, 2H), 8.35 (d, J=6.6 Hz, 2H), 8.23 (d, J=7.9 Hz, 2H), 7.70 (d, J=3.6 Hz, 1H), 7.45-7.28 (m, 5H), 7.16-7.13 (m, 1H).

(3) Synthesis of 4'-(2'''-thienyl)-2,2':6',2''-terpyridine-6,6''-dicarbonitrile [Compound (3)]

To 300 ml of CH$_2$Cl$_2$, the compound (2) (8.69 g, 25 mmol) and (CH$_3$)$_3$SiCN (24.8 g, 250 mmol) were added and stirred for 20 minutes at room temperature. Then, 100 mmol of benzoyl chloride was added dropwise thereto little by little over the period of about 20 minutes. After the reaction solution was stirred for 20 hours at room temperature, half of the solvent was removed under reduced pressure. To the remaining solution, 600 ml of 10% K$_2$CO$_3$ aqueous solution was added, stirred for 1 hour at room temperature, and a precipitate was obtained by filtration. Thereafter, the precipitate was washed thoroughly with water, further washed with chilled CH$_2$Cl$_2$, then vacuum dried, thus the compound (3) was obtained. The yield was 98.5%. The product was confirmed to be the target compound by $^1$H NMR.

$^1$H NMR (DMSO-d$_6$): δ 8.95 (d, J=7.9 Hz, 2H), 8.62 (s, 2H), 8.32-8.26 (m, 2H), 8.19 (d, J=7.6 Hz, 2H), 8.07 (d, J=3.6 Hz, 1H), 7.86 (d, J=5.1 Hz, 1H), 7.28-7.31 (m, 1H)

(4) Synthesis of 4'-(2'''-thienyl)-2,2':6',2''-terpyridine-6,6''-dicarboxylate dimethyl [Compound (4)]

To a mixed solvent of H$_2$SO$_4$ (45 ml), CH$_3$COOH (45 ml) and H$_2$O (12 ml), 4.40 g of the compound (3) was added, and stirred for 48 hours at 75 to 80° C. The reaction solution was added to 400 g of ice and stirred, then a precipitate was obtained by filtration. The precipitate was washed thoroughly with water and ethanol, then vacuum dried, thus 4.85 g of a hydrolysate was obtained.

To 400 ml of dried methanol, which had been cooled with ice-water, 8 g of SOCl$_2$ was added, and stirred for 15 minutes. Then, 4.85 g of the hydrolysate obtained above was added thereto, and the solution was refluxed for 20 hours while stirring. The solvent was removed under reduced pressure, and the product was dissolved in 350 ml of CHCl$_3$. The organic layer was washed thoroughly with 15% NaHCO$_3$ aqueous solution, then dried with Na$_2$SO$_4$. The solvent was removed under reduced pressure, and the product was purified with a silica gel column (developing solvent: CH$_2$Cl$_2$—CH$_3$OH=99:1 w/w). The product was recrystallized from toluene, thus the compound (4) was obtained. The yield was 48.1%.

Results of elementary analysis (C$_{23}$H$_{17}$N$_3$O$_4$S)

Calculated value (%), C=64.03, H=3.97, N=9.74.Measured value (%), C=63.76, H=3.83, N=9.52.

Furthermore, the product was confirmed to be the target compound by $^1$H NMR.

$^1$H NMR (CDCl$_3$): δ 8.16 (d, J=7.8 Hz, 2H), 8.78 (s, 2H), 8.20 (d, J=7.6 Hz, 2H), 8.03 (t, J=7.8 Hz, 2H), 7.82 (d, J=3.6 Hz, 1H), 7.49 (d, J=5.1 Hz, 1H), 7.22-7.19 (m, 1H), 4.08 (s, 6H)

(5) Synthesis of 4'-(2'''-thienyl)-2,2':6',2''-terpyridine-6,6''-dihydroxymethyl [Compound (5)]

To 200 ml of dried ethanol, the compound (4) (2.89 g, 6.7 mmol) and 1.05 g of NaBH$_4$ were added, stirred for 3 hours at room temperature, then the solution was refluxed for 1 hour. The solvent was removed under reduced pressure, and the product was added to 100 ml of saturated NaHCO$_3$ aqueous solution and heated until it boiled while stirring. After the solution was cooled, a precipitate was obtained by filtration. The precipitate was washed thoroughly with water, then vacuum dried. The product was dissolved in 200 ml of THF, and a trace amount of insoluble substances was removed by filtration, then the solvent was removed under reduced pressure. The product was washed thoroughly with acetonitrile and vacuum dried, thus the compound (5) was obtained. The yield was 72.2%. The product was confirmed to be the target compound by $^1$H NMR.

$^1$H NMR (DMSO-d$_6$): δ 8.63 (s, 2H), 8.50 (d, J=7.3 Hz, 2H) 8.03 (t, J=7.3 Hz, 2H), 7.93 (d, J=3.6 Hz, 1H), 7.82 (d, J=5.1 Hz, 1H), 7.61 (d, J=7.1 Hz, 2H), 7.28-7.31 (m, 1H), 4.74 (s, 4H).

(6) Synthesis of 4'-(5'''-nitro-2'''-thienyl)-2,2':6',2''-terpyridine-6,6''-dihydroxymethyl [Compound (6)]

The compound (5) (1.50 g, 4 mmol) was added to 15 ml of acetic anhydride, stirred for 1 hour at room temperature, and further stirred for 1 hour at 60° C. The reaction solution was cooled to room temperature, and a mixed solution of 2 g of fuming nitric acid and 20 ml of acetic acid was added and stirred for 24 hours at room temperature. The reaction solution was added to 200 ml of water, stirred overnight, and extracted with CHCl$_3$ (4×50 ml). The CHCl$_3$ solution was washed with water and dried with Na$_2$SO$_4$, then the solvent was removed under reduced pressure. The product was dissolved in 100 ml of ethanol, and 4 g of KOH and 5 ml of water were added and stirred for 24 hours at room temperature. The solvent was removed under reduced pressure. The product was washed with water and vacuum dried, thus the compound (6) was obtained. The yield was 75.1%. The product was confirmed to be the target compound by $^1$H NMR.

$^1$H NMR (DMSO-d$_6$): δ 8.57 (s, 2H), 8.40 (d, J=7.3 Hz, 2H), 8.15 (d, J=3.6 Hz, 1H), 7.96 (t, J=7.5 Hz, 2H), 7.89 (d, J=5.1 Hz, 1H), 7.57 (d, J=7.1 Hz, 2H), 5.50 (sb, 2H), 4.72 (s, 4H).

(7) Synthesis of 4'-(5'''-nitro-2'''-thienyl)-2,2':6',2''-terpyridine-6,6''-dibromomethyl-[Compound (7)]

The compound (6) (1.26 g, 3 mmol) was dissolved in a mixed solvent of THF (120 ml) and DMF (15 ml), and 2.40 g of PBr$_3$ was added, then the solution was refluxed for 5 hours while stirring. After the solvent was removed under reduced pressure, 200 ml of CHCl$_3$ was added to the product, and the CHCl$_3$ solution was washed with 10% Na$_2$CO$_3$ aqueous solution (4×80 ml). The organic layer was dried with Na$_2$SO$_4$, and the solvent was removed under reduced pressure. The obtained residue was washed thoroughly with hexane and vacuum dried, thus the compound (7) was obtained. The yield was 70.1%. The product was confirmed to be the target compound by $^1$H NMR.

$^1$H NMR (DMSO-d$_6$): δ 8.55 (s, 2H), 8.46 (d, J=7.3 Hz, 2H), 8.16 (d, J=4.4 Hz., 1H), 7.97 (t, J=7.5 Hz, 2H), 7.88 (d, J=5.1 Hz, 1H), 7.65 (d, J=7.1 Hz, 2H), 4.80 (s, 4H).

(8) Synthesis of tetraethyl N,N,N',N'-[4'-(5'''-nitro-2'''-thienyl)-2,2':6',2''-terpyridine-6,6''-diyl)bis(methylenenitrilo)]tetrakis(acetate) [Compound (8)]

The compound (7) (1.09 g, 2 mmol) was dissolved in 150 ml of CH$_3$CN, and 4.1 mmol of diethyliminodiacetate and 20 mmol of K$_2$CO$_3$ were added, then the solution was refluxed for 24 hours while stirring. The insoluble substances were removed by filtration, and the solvent was removed under reduced pressure. Then, 200 ml of CHCl$_3$ was added to the product, and the CHCl$_3$ solution was washed with saturated Na$_2$SO$_4$ aqueous solution (4×100 ml). The organic layer was dried with Na$_2$SO$_4$, and the solvent was removed under reduced pressure. Then the oily product was purified with a silica gel column (developing solvent: CH$_3$COOEt-CH$_3$OH-THF=90:6:4 w/w/w), thus the compound (8) was obtained. The yield was 50.1%. The product was confirmed to be the target compound by $^1$H NMR.

$^1$H NMR (CDCl$_3$): δ 8.70 (s, 2H), 8.51 (d, J=7.8 Hz, 2H), 7.99 (d, J=4.4 Hz, 1H), 7.87 (t, J=7.6 Hz, 2H), 7.74 (d, J=4.4 Hz, 1H), 7.66 (d, J=7.8 Hz, 2H), 4.19 (q, J=7.2 Hz, 8H), 4.08 (s, 4H), 3.71 (s, 8H), 1.26 (t, J=7.2 Hz, 12H).

(9) Synthesis of tetraethyl N,N,N',N'-[4'-(5'''-amino-2'''-thienyl)-2,2':6',2''-terpyridine-6,6''-diyl)bis(methylenenitrilo)]tetrakis(acetate) [compound (9)]

After the compound 8 (0.76 g, 1 mmol) was dissolved in 70 ml of EtOH, SnCl$_2$.2H$_2$O (1.32 g, 6 mmol) was added and stirred for 1 hour at 70 to 80° C. After the solution was cooled to room temperature, it was poured into a solution of H$_2$O (100 ml) and DTPA (5 g), which had been cooled in an ice water bath, and stirred. Then, 20 ml of saturated NaHCO$_3$ aqueous solution was added to the solution and stirred for 30 minutes at room temperature. The aqueous solution was extracted with CHCl$_3$ (3×100 ml), and the organic layer was dried with Na$_2$SO$_4$. The solvent was removed under reduced pressure, and the residue was vacuum dried, thus the compound (9) was obtained. The yield was 93.5%. The product was confirmed to be the target compound by $^1$H NMR.

$^1$H NMR (CDCl$_3$): δ 8.44 (s, 2H), 8.41 (d, J=7.2 Hz, 2H), 7.78 (t, J=7.6 Hz, 2H), 7.56 (d, J=7.2 Hz, 2H), 7.38 (d, J=4.2 Hz, 1H), 6.17 (d, J=4.2 Hz, 1H), 4.19 (q, J=7.2 Hz, 8H), 4.08 (s, 4H), 3.74 (s, 8H), 1.26 (t, J=7.2 Hz, 12H)

(10) Synthesis of tetraethyl N,N,N',N'-[4'-(5'''-amino-2'''-thienyl)-2,2':6',2''-terpyridine-6,6''-diyl)bis(methylenenitrilo)]tetrakis(acetate) [ATTTA, Compound (10)]

The compound (9) (586 mg, 0.8 mmol) was dissolved in a solution of EtOH (40 ml), H$_2$O (5 ml) and KOH (1.2 g) and stirred for 24 hours at room temperature, then the solvent was removed under reduced pressure. After the residue was dissolved in 60 ml of water, 1% CF$_3$COOH aqueous solution was added dropwise thereto little by little while stirring to adjust the pH of the solution to about 1. After the solution was stirred for 3 hours at room temperature, a precipitate was obtained by filtration. The precipitate was washed well with 0.5% CF$_3$COOH aqueous solution and vacuum dried, thus the compound (10) was obtained. The yield was 90.0%.

Results of elementary analysis (C$_{29}$H$_{28}$N$_6$O$_8$S):

Calculated value (%), C=56.13; H=4.55; N=13.54. Measured value (%), C=55.94; H=4.38; N=13.62.

Furthermore, the product was confirmed to be the target compound by $^1$H NMR.

¹H NMR (DMSO-d₆): δ 8.10 (s, 2H), 8.04 (d, J=7.2 Hz, 2H), 7.45 (t, J=7.2 Hz, 2H), 7.31 (d, J=7.2 Hz, 2H), 7.25 (d, J=4.2 Hz, 1H), 6.14 (d, J=4.2 Hz, 1H), 4.00 (s, 4H), 3.51 (s, 8H).

Example 2

Synthesis of [4'-(5'''-amino-2'''-thienyl)-2,2':6',2''-terpyridine-6,6''-diyl)bis(methylene-nitrilo)]-N:N',N:N'-bis(3,6-dioxa-triethylene) (abbreviated as ATTBB)

(1) Synthesis of [4'-(5'''-nitro-2'''-thienyl)-2,2':6',2''-terpyridine-6,6''-diyl)bis(methylene-nitrilo)]-N:N',N:N'-bis(3,6-dioxa-triethylene)

4'-(5'''-amino-2'''-thienyl)-2,2':6',2''-terpyridine-6,6''-dibromomethyl (1.09 g, 2 mmol) was dissolved in 150 ml of CH₃CN, and 2.1 mmol of 4,13-diaza-18-crown 6-ether and 20 mmol of K₂CO₃ were added, then the solution was refluxed for 24 hours while stirring. The insoluble substances were removed by filtration, and the solvent was removed under reduced pressure. The product was purified with a silica gel column (developing solvent: CH₂Cl₂—CH₃OH=9:1 w/w). The yield was 65.3%. The product was confirmed to be a complex of KBr with the target compound (1:1, M.W.=765.727) by FAB-MS.

FAB-MS: measured value: 766

(2) Synthesis of [4'-(5'''-amino-2'''-thienyl)-2,2':6',2''-terpyridine-6,6''-diyl)bis(methylene-nitrilo)]-N:N',N:N'-bis(3,6-dioxa-triethylene) (abbreviated as ATTBB)

The KBr complex obtained in the above-mentioned (1) (765.7 mg, 1 mmol) was dissolved in 50 ml of dried methanol, and 150 mg of 10% Pd/C catalyst was added, then 40 mg of NaBH₄ was added. The mixture was stirred for 2 hours at room temperature, and the insoluble substances were removed by filtration. The solvent was removed under reduced pressure, and the product was dissolved in 30 ml of water. The aqueous solution was extracted with CHCl₃ (4×50 ml), and dried with Na₂SO₄. The solvent was removed under reduced pressure, and the residue was vacuum dried. The yield was 40.3%. The product was confirmed to be a complex of KBr with the target compound (1:1, M.W.=735.744) by FAB-MS.

FAB-MS: measured value: 736

Example 3

Synthesis of N,N,N',N'-[2,6-bis(3'-aminomethyl-1'-pyrazolyl)-4-(5''-amino-2''-thienyl) pyridine]tetrakis (acetate) (Abbreviated as BAPTA)

(1) Synthesis of 2,6-dibromo-4-(2' thienyl)pyridine [Compound (11)]

4-amino-2,6-dibromopyridine (3.25 g, 12.9 mmol) and 12.9 g of thiophene were dissolved in 250 ml of acetic acid, and 1.93 g of isoamyl nitrate was added while stirring. The mixture was stirred for 24 hours at room temperature, and further stirred for 3 hours at about 45° C. The solvent was removed under reduced pressure, and the residue was neutralized with 40 ml of 10% K₂CO₃ aqueous solution, then extracted with CHCl₃ (4×60 ml). The organic layer was dried with Na₂SO₄, and the solvent was removed under reduced pressure, then the residue was purified with a silica gel column (developing solvent: CH₂Cl₂—CH₃OH=9:1 w/w). Furthermore, the product was recrystallized with methanol twice, thus the compound (11) was obtained. The yield was 47.9%.

Results of elementary analysis (C₉H₅NBr₂S):
Calculated value (%), C=33.88; H=1.58; N=4.39. Measured value (%), C=33.46; H=1.46; N=4.23.

Furthermore, the product was confirmed to be the target compound by ¹H NMR.

¹H NMR (CDCl₃): δ7.60 (s, 2H), 7.50-7.48 (m, 2H), 7.16-7.13 (m, 1H).

(2) Synthesis of 2,6-bis(3'-methoxycarbonyl-1'-pyrazolyl)-4-(2''-thienyl)pyridine [compound (12)]

In 100 ml of dried THF, 10.1 g of 3-methoxycarbonyl pyrazole was dissolved, and 3.12 g of metal potassium was added thereto, and stirred at about 60° C. until all the metal was dissolved. The compound (11) (6.38 g, 20 mmol) was added to the solution, which was refluxed for 1 week while stirring. The solvent was removed under reduced pressure, and the residue was extracted with CHCl₃ (6×150 ml), then the solvent was removed under reduced pressure again. The product was purified with a silica gel column (developing solvent: CH₂Cl₂—CH₃OH=9:1 w/w). Furthermore, the product was recrystallized with benzene, thus the compound (12) was obtained. The yield was 45.5%.

Results of elementary analysis (C₁₉H₁₅N₅O₄S)—:
Calculated value (%), C=55.74; H=3.69; N=17.10. Measured value (%), C=55.47, H=3.62, N=16.82.

Furthermore, the product was confirmed to be the target compound by ¹H NMR.

¹H NMR (CDCl₃): δ 8.60 (d, J=2.7 Hz, 2H), 8.22 (s, 2H), 7.79 (d, J=3.6 Hz, 1H), 7.53 (d, J=5.0 Hz, 1H), 7.20-7.18 (m, 1H), 7.03 (d, J=2.7 Hz, 2H), 4.01 (s, 6H).

(3) Synthesis of 2,6-bis(3'-hydroxymethyl-1'-pyrazolyl)-4-(2''-thienyl)pyridine [Compound (13)]

To 300 ml of dried THF, 1.30 g of LiAlH₄ and the compound (12) (2.72 g, 6.64 mmol) were added and stirred for 4 hours at room temperature. Thereto was added 1.1 ml of water, subsequently 1.1 ml of 15% NaOH and 4.5 ml of water were added dropwise little by little and stirred for 30 minutes at room temperature. Then, the precipitate was removed by filtration, and the precipitate was further washed with a small amount of THF, then the THF solutions were combined. The solvent was removed under reduced pressure, and the residue was washed thoroughly with acetonitrile, then vacuum dried, thus the compound (13) was obtained. The yield was 71.3%. The product was confirmed to be the target compound by ¹H NMR.

¹H NMR (DMSO-d₆): δ 8.88 (d, J=2.6 Hz, 2H), 7.96 (d, J=3.6 Hz, 1H), 7.90 (s, 2H), 7.85 (d, J=5.1 Hz, 1H), 7.29-7.26 (m, 1H), 6.60 (d, J=2.5 Hz, 2H), 4.58 (s, 4H).

(4) Synthesis of 2,6-bis(3'-hydroxymethyl-1'-pyrazolyl)-4-(5''-nitro-2''-thienyl)pyridine [Compound (14)]

The compound (13) (1.59 g, 4.5 mmol) was added to 20 ml of acetic anhydride, stirred for 1 hour at room temperature, and further stirred for 1 hour at 60° C. The reaction solution was cooled to room temperature, and a mixed solution of 1.5 g of fuming nitric acid and 20 ml of acetic acid was added thereto, then stirred for 24 hours at room temperature. The reaction solution was added to 200 ml of water, stirred overnight, then extracted with $CHCl_3$ (4×50 ml). The $CHCl_3$ solution was washed with water and dried with $Na_2SO_4$, then the solvent was removed under reduced pressure. The residue was vacuum dried and purified with a silica gel column (developing solvent: $CH_2Cl_2$—$CH_3OH$=9:1 w/w). The product was dissolved in 100 ml of ethanol, and 4 g of KOH and 5 ml of water were added, and stirred for 24 hours at room temperature. The solvent was removed under reduced pressure, and the residue was washed with water, then vacuum dried, thus the compound (14) was obtained. The yield was 70.4%. The product was confirmed to be the target compound by $^1$H NMR.

$^1$H NMR (DMSO-$d_6$): δ9.01 (d, J=2.6 Hz, 2H), 8.15 (d, J=3.6 Hz, 1H), 7.89 (s, 2H), 7.84 (d, J=5.1 Hz, 1H), 6.71 (d, J=2.5 Hz, 2H), 4.57 (s, 4H)

(5) Synthesis of 2,6-bis(3'-bromomethyl-1'-pyrazolyl) -4-(5"-nitro-2"-thienyl)pyridine [Compound (15)]

The compound (14) (1.59 g, 4 mmol) was dissolved in 200 ml of THF, and 3.20 g of $PBr_3$ was added thereto, then the solution was refluxed for 4 hours while stirring. After the solvent was removed under reduced pressure, 200 ml of $CHCl_3$ was added to the residue, then the $CHCl_3$ solution was washed with 10% $NaHCO_3$ aqueous solution (4×80 ml). The organic layer was dried with $Na_2SO_4$, and the solvent was removed under reduced pressure. The residue was washed thoroughly with hexane and vacuum dried, thus the compound (15) was obtained. The yield was 94.1%. The product was confirmed to be the target compound by $^1$H NMR.

$^1$H NMR (CDCl$_3$): δ 9.04 (d, J=2.6 Hz, 2H), 8.17 (d, J=3.6 Hz, 1H), 7.87 (s, 2H), 7.81 (d, J=5.1 Hz, 1H), 6.73 (d, J=2.5 Hz, 2H), 4.66 (s, 4H).

(6) Synthesis of tetraethyl N,N,N',N'-[2,6-bis(3'-aminomethyl-1'-pyrazolyl)-4-(5"-nitro-2"-thienyl) pyridine]tetrakis(acetate) [Compound (16)]

The compound (15) (1.05 g, 2 mmol) was dissolved in 150 ml of $CH_3CN$, and 4.1 mmol of diethyl-iminodiacetic acid and 20 mmol of $K_2CO_3$ were added, then the solution was refluxed for 24 hours while stirring. The insoluble substances were removed by filtration, and the solvent was removed under reduced pressure. Then, 200 ml of $CHCl_3$ was added to the residue, and the $CHCl_3$ solution was washed with saturated $Na_2SO_4$ aqueous solution (4×100 ml). The organic layer was dried with $Na_2SO_4$, and the solvent was removed under reduced pressure. Then the oily product was purified with a silica gel column (developing solvent: $CH_3COOEt$-$CH_2Cl_2$=9:1 w/w), thus the compound (16) was obtained. The yield was 50.0%. The product was confirmed to be the target compound by $^1$H NMR.

$^1$H NMR (CDCl$_3$): δ9.03 (d, J=2.6 Hz, 2H), 8.14 (d, =3.6 Hz, 1H), 7.88 (s, 2H), 7.81 (d, J=5.1 Hz, 1H), 6.72 (d, J=2.5 Hz, 2H), 4.18 (q, J=7.2 Hz, 8H), 4.08 (s, 4H), 3.65 (s, 8H), 1.26 (t, J=7.2 Hz, 12H).

(7) Synthesis of tetraethyl N,N,N',N'-[2,6-bis(3'-aminomethyl-1'-pyrazolyl)-4-(5"-amino-2"-thienyl) pyridine]tetrakis(acetate) [Compound (17)]

The compound (16) (741 mg, 1 mmol) was dissolved in 70 ml of EtOH, and $SnCl_2.2H_2O$ (1.32 g, 6 mmol) was added thereto, then stirred for 1 hour at 70 to 80° C. After the solution was cooled to room temperature, it was poured into a solution of $H_2O$ (100 ml) and DTPA (5 g), which had been cooled in an ice water bath, and stirred. Then, 20 ml of saturated $NaHCO_3$ aqueous solution was added to the solution and stirred for 30 minutes at room temperature. Then, the solution was extracted with $CHCl_3$ (3×100 ml), and the organic layer was dried with $Na_2SO_4$. The solvent was removed under reduced pressure, and the product was vacuum dried, thus the compound (17) was obtained. The yield was 91.7%. The product was confirmed to be the target compound by $^1$H NMR.

$^1$H NMR (CDCl$_3$): δ 8.81 (d, J=2.6 Hz, 2H), 7.58 (s, 2H), 7.38 (d, J=3.6 Hz, 1H), 6.72 (d, J=2.5 Hz, 2H), 6.52 (d, J=5.1 Hz, 1H), 4.18 (q, J=7.2 Hz, 8H), 4.08 (s, 4H), 3.65 (s, 8H), 1.26 (t, J=7.2 Hz, 12H).

(8) Synthesis of N,N,N',N'-[2,6-bis(3'-aminomethyl-1'-pyrazolyl)-4-(5"-amino-2"-thienyl)pyridine]tetrakis(acetate) [BAPTA, Compound (18)]

The compound (17) (569 mg, 0.8 mmol) was dissolved in a solution of EtOH (40 ml), $H_2O$ (5 ml) and KOH (1.2 g), stirred for 24 hours at room temperature, and the solvent was removed under reduced pressure. After the residue was dissolved in 60 ml of water, 1% $CF_3COOH$ aqueous solution was added dropwise thereto little by little while stirring to adjust the pH of the solution to about 1. After the solution was stirred for 3 hours at room temperature, a precipitate was obtained by filtration. The precipitate was washed thoroughly with 0.5% $CF_3COOH$ aqueous solution and vacuum dried, thus the compound (18) was obtained. The yield was 91.3%.

Results of elementary analysis ($C_{25}H_{26}N_8O_8S$):

Calculated value (%), C=50.17; H=4.38; N=18.71. Measured value (%), C=50.29; H=4.25; N=18.48.

Furthermore, the product was confirmed to be the target compound by $^1$H NMR.

$^1$H NMR (DMSO-$d_6$): δ 9.16 (d, J=2.6 Hz, 2H), 7.72 (s, 2H), 7.42 (d, J=3.6 Hz, 1H), 6.76 (d, J=2.5 Hz, 2H), 6.59 (d, J=5.1 Hz, 1H), 4.00 (s, 4H), 3.55 (s, 8H).

Example 4

Synthesis of [2,6-bis(3'-aminomethyl-1'-pyrazolyl)-4-(5"-amino-2"-thienyl)pyridine]-N:N',N:N'-bis(3,6-dioxa-triethylene) (Abbreviated as BAAPB)

(1) Synthesis of [2,6-bis(3'-aminomethyl-1'-pyrazolyl)-4-(5"-nitro-2"-thienyl)pyridine]-N:N',N:N'-bis(3,6-dioxa-triethylene)

2,6-bis(3'-bromomethyl-1'-pyrazolyl)-4-(5"-nitro-2"-thienyl)pyridine (0.80 g, 2 mmol) was dissolved in 100 ml of $CH_3CN$, and 2.1 mmol of 4,13-diaza-18-crown 6-ether and 20 mmol of $K_2CO_3$ were added thereto, then the solution was refluxed for 24 hours while stirring. The insoluble substances were removed by filtration, and the solvent was removed under reduced pressure. The product (residue) was purified with a silica gel column (developing solvent: $CH_2Cl_2$— $CH_3OH$=9:1 w/w) The yield was 53.8%. The product was confirmed to be a complex of KBr with the target compound (1:1, M.W.=743.667) by FAB-MS.

FAB-MS: measured value: 744

(2) Synthesis of [2,6-bis(3'-aminomethyl-1'-pyrazolyl)-4-(5''-amino-2''-thienyl)pyridine]-N:N',N:N'-bis(3,6-dioxa-triethylene) (BAAPB)

TABLE 1

| Complex | Absorption maximum wavelength (nm) | Molar extinction coefficient ($M^{-1}cm^{-1}$) | Fluorescence maximum wavelength (nm) | Fluorescence quantum yield | Fluorescence lifetime (ms) |
| --- | --- | --- | --- | --- | --- |
| ATTTA-$Eu^{3+}$ | 336 | $2.50 \times 10^4$ | 615 | 0.15 | 1.30 |
| ATTBB-$Eu^{3+}$ | 336 | $2.61 \times 10^4$ | 615 | 0.16 | 1.34 |
| BAPTA-$Eu^{3+}$ | 324 | $2.60 \times 10^4$ | 620 | 0.12 | 1.40 |
| BAAPB-$Eu^{3+}$ | 325 | $2.66 \times 10^4$ | 620 | 0.13 | 1.45 |

The KBr complex obtained in the above-mentioned (1) (743.7 mg, 1 mmol) was dissolved in 50 ml of dried methanol, and 150 mg of 10% Pd/C catalyst was added thereto. Then, 40 mg of $NaBH_4$ was added thereto and stirred for 2 hours at room temperature. The insoluble substances were removed by filtration, and the solvent was removed under reduced pressure, then the residue was dissolved in 30 ml of water. The aqueous solution was extracted with $CHCl_3$ (4×50 ml), and dried with $Na_2SO_4$. The solvent was removed under reduced pressure, and the residue was vacuum dried, thus the target compound (complex) was obtained. The yield was 52.4%. The product was confirmed to be a complex of KBr with BAAPB (1:1, M.W.=713.684) by FAB-MS.

FAB-MS: measured value: 714

Example 5

Synthesis of Complex of Various Ligands and Europium

With respect to the synthesis of europium complexes of ATTTA and BAPTA among the 4 ligands obtained in Examples 1 to 4, first, the ligands were dissolved in 0.05 M borate buffer solution (pH 9.1), subsequently, the same molar amount of $EuCl_3$ was added and stirred for 1 hour at room temperature, whereby solutions of complexes, ATTTA-$Eu^{3+}$ and BAPTA-$Eu^{3+}$ were obtained.

With respect to the synthesis of europium complexes of ATTBB and BAAPB, first, ATTBB.KBr or BAAPB.KBr was dissolved in ethanol, subsequently, 2-fold molar amount of $EuCl_3$ was added, and the solution was refluxed for 2 hours while stirring. The solvent was removed under reduced pressure, the residue was dissolved in $CHCl_3$, and the insoluble substances were removed by filtration. Then, the solvent was removed under reduced pressure, and the residue was vacuum dried, thus a complex ATTBB-$Eu^{3+}$ or BAAPB-$Eu^{3+}$ was obtained.

Example 6

Evaluation of Fluorescence Characteristics of 4 Europium Complexes

The 4 complexes obtained in Example 5 were dissolved in 0.05M borate buffer solution (pH 9.1), and $1.0 \times 10^{-6}$M solutions were prepared. By using these solutions, the UV spectrum, fluorescence spectrum, fluorescence quantum yield, molar extinction coefficient and fluorescence lifetime of each solution were measured. The results are shown in Table 1. Also, the fluorescence spectra of ATTTA-$Eu^{3+}$ are shown in FIG. 1.

As is clear from Table 1, it is shown that any of the 4 complexes has a strong fluorescence and a long fluorescence lifetime and can be used effectively as a labeling agent for time-resolved fluorescence assay.

Example 7

Time-Resolved Fluorescence Assay Using Complex According to the Present Invention By using the complex ATTTA-$Eu^{3+}$, the measurement sensitivity of the complex by a time-resolved fluorescence assay was measured. The solvent for diluting the complex was 0.05 M Tris-HCl buffer solution (pH 7.8), and the measurement device was the Victor 1420 time-resolved fluorometer (PerkinElmer Life Sciences, Inc.). The measurement conditions were as follows: the excitation wavelength=340 nm, the measurement wavelength=615 nm, the delay time=0.2 ms, the window time=0.4 ms, the cycling time=1.0 ms.

Figure 2:
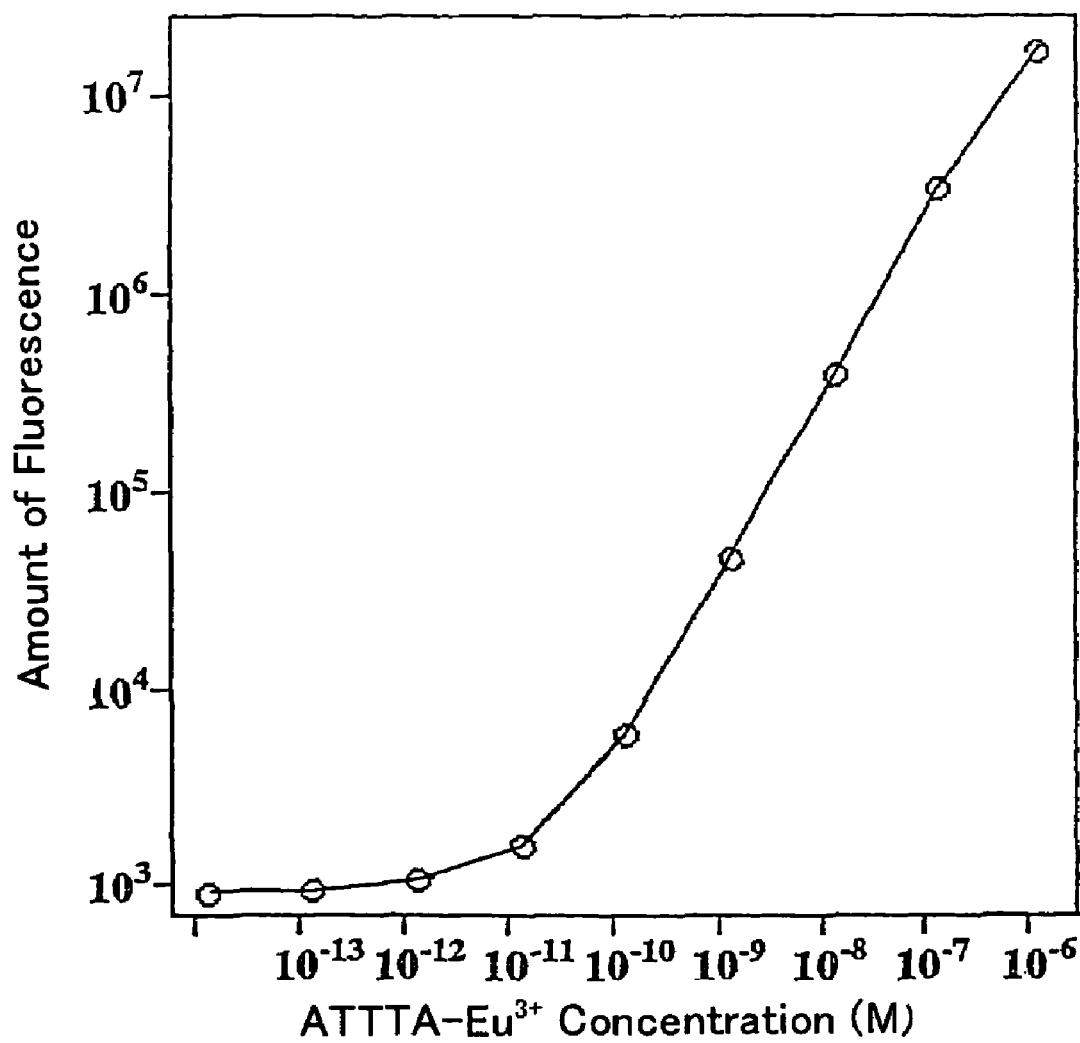
FIG. 2 is a diagram showing the results of the time-resolved fluorescence assay for the diluted solution of ATTTA-Eu$^{3+}$ of the present invention.

FIG. 2 shows the results of the time-resolved fluorescence assay for the diluted solution of ATTTA-$Eu^{3+}$.

From the result of calculation by using the 2-fold standard deviation of the background signal, it was found that the minimum detection limit of the time-resolved fluorescence assay using ATTTA-$Eu^{3+}$ was $8.0 \times 10^{-13}$ M. This result shows that the time-resolved fluorescence assay using ATTTA-$Eu^{3+}$ is very highly sensitive.

Example 8

Labeling of Protein, Streptavidin (SA) Using ATTTA-$Eu^{3+}$

Before labeling was performed, first, by using 2,4,6-trichloro-1,3,5-triazine, activation of the amino group of ATTTA was performed. The method is as follows.

ATTTA (124 mg, 0.2 mmol) was dissolved in 5 ml of 0.5 M sodium acetate aqueous solution (pH 4.9), and 1 ml of an acetone solution containing 2,4,6-trichloro-1,3,5-triazine (36 mg, 0.2 mmol) was added dropwise while stirring, then the solution was stirred for 30 minutes at room temperature. The pH of the reaction solution was adjusted to about 1 with 1 M HCl, and the precipitate was recovered by centrifugation, washed with an HCl solution, which had been diluted to 100-fold, then vacuum dried. By this method, a derivative of ATTTA having an active substituent group, (4,6-dichloro-1,3,5-triazine-2-yl) group was obtained. The obtained compound did not need to be purified and could be directly used for labeling a protein.

After dissolving 5 mg of SA in 10 ml of 0.1M sodium carbonate buffer solution (pH 9.1), 10 mg of the ATTTA derivative having (4,6-dichloro-1,3,5-triazine-2-yl) group was added, and continuously stirred for 1 hour at room temperature. The unreacted labeling reagent was separated from the labeled protein by gel filtration of the reaction solution. A Sephadex G-50 column (1.0×40 cm) was used, and the resolution was performed with 0.05 M $NH_4HCO_3$ aqueous solution. A small amount of the labeled protein solution was taken, and the concentration of ATTTA in the labeled SA solution was measured by fluorescence titration with the use of a standard $EuCl_3$ aqueous solution. Then, the labeling ratio of the labeled SA was calculated, whereby a solution of $SA(ATTTA)_{21}$ was obtained. To the solution of $SA(ATTTA)_{21}$, $EuCl_3$ of 1.5-fold molar amount of ATTTA was added and stirred. Then, 25 mg of $NaN_3$ was added as an antiseptic and 50 mg of BSA (bovine serum albumin) was added for preventing the labeled protein from adhering to the container. Then, the solution was stored at −20° C. When the solution is used for a time-resolved fluoroimmunoassay, use it after diluting to 1000-fold with 0.05 M Tris-HCl buffer solution (pH 7.8) containing 0.2% BSA, 0.9% NaCl and 0.1% $NaN_3$.

Example 9

Time-Resolved Fluoroimmunoassay for CEA (Carcinoembryonic Antigen) in Human Serum Using $SA(ATTTA-Eu^{3+})_{21}$ An assay was performed by using a 96-well microtiter plate. Specific operation procedures are as follows.

(i) Preparation of biotinylated antibody: After 0.5 ml (2.4 mg/ml) of a rabbit anti-human CEA antibody solution (Dako-immunoglobulins, Denmark) was dialyzed twice against 3 L of saline at 4° C. for 24 hours each, 0.5 ml of purified water, 8.4 mg of $NaHCO_3$ and 6 mg of sulfosuccinimidyl-6-(biotinamido)hexanoate (NHS-LC-Biotin, Pierce Chem. Co.) were added. Then, the solution was stirred for 1 hour at room temperature, and incubated at 4° C. for 24 hours. After the reaction solution was dialyzed twice against 3 L of 0.1 M $NaHCO_3$ solution containing 0.25 g of $NaN_3$ at 4° C. for 24 hours each, 10 mg of BSA was added, and the solution was stored at −20° C. until it was used for an immunoassay. When the solution is used for an immunoassay, use it after diluting to 100-fold with 0.05 M Tris-HCl buffer solution (pH 7.8) containing 0.2% BSA, 0.9% NaCl and 0.1% $NaN_3$.

(ii) Coating of 96-well microtiter plate: After a goat anti-human CEA polyclonal antibody was diluted to 8 μg/ml with 0.1 M carbonate buffer solution (pH 9.6), a 60 μl aliquot of the solution was dispensed into a 96-well microtiter plate made of transparent polystyrene (FluoroNunc plate) and incubated for 24 hours at 4° C. Subsequently, the plate was washed twice with 0.05 M Tris-HCl buffer solution (pH 7.8) containing 0.05% Tween 20 (Buffer 1), and further washed once with 0.05M Tris-HCl buffer solution (pH 7.8) (Buffer 2).

(iii) Immunoassay for CEA: Into each well of the antibody coated 96-well microtiter plate, a 50 μl aliquot of CEA standard solution (Seikagaku co.) was dispensed, and incubated for 1 hour at 37° C. Then, the plate was washed twice with Buffer 1 and once with Buffer 2. Into the respective wells, a 50 μl aliquot of the biotinylated rabbit anti-human CEA antibody was dispensed, and incubated for 1 hour at 37° C. Then, the plate was washed twice with Buffer 1 and once with Buffer 2. Into the respective wells, a 50 μl aliquot of the SA(ATTTA-$Eu^{3+})_{21}$ solution was dispensed, and incubated for 1 hour at 37° C. Then, the plate was washed four times with Buffer 1, and continuously used for a solid phase time-resolved fluorescence assay.

The device for time-resolved fluorescence assay used in this measurement was the Victor 1420 time-resolved fluorometer (PerkinElmer Life Sciences, Inc.), and the measurement conditions were as follows: the excitation wavelength=340 nm, the measurement wavelength=615 nm, the delay time=0.2 ms, the window time=0.4 ms, the cycling time=1.0 ms.

Figure 3:
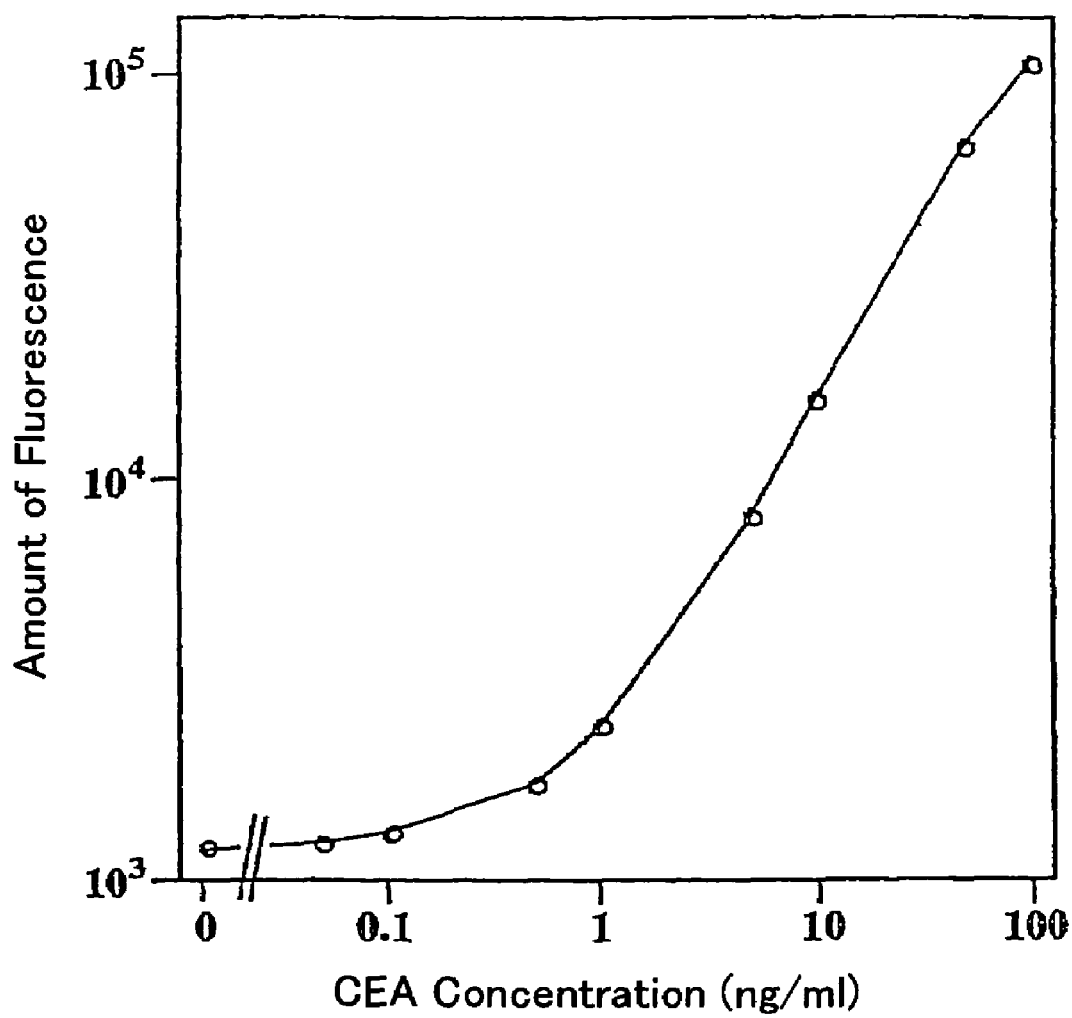
FIG. 3 is a diagram showing the calibration curve obtained by the time-resolved fluoroimmunoassay of the present invention.

The calibration curve obtained by the above immunoassay is shown in FIG. 3. In the case where the background signal+3 SD (standard-deviation) was assigned to the detection limit, the detection limit of this method was 60 pg/ml. This value shows that this method is about twice as sensitive as a radioimmunoassay, an enzyme immunoassay or the like, which is commercially available.

Example 10

Production of Compound Represented by General Formula [1-1]

A compound represented by the general formula [1-1] in which R is a 4'-amino-biphenyl-4-yl group was produced according to the reaction scheme shown below.

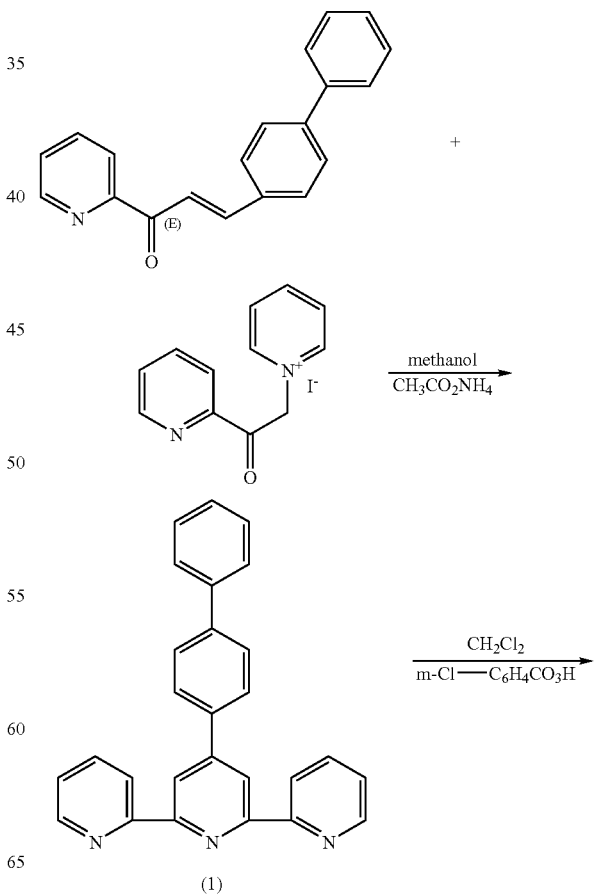

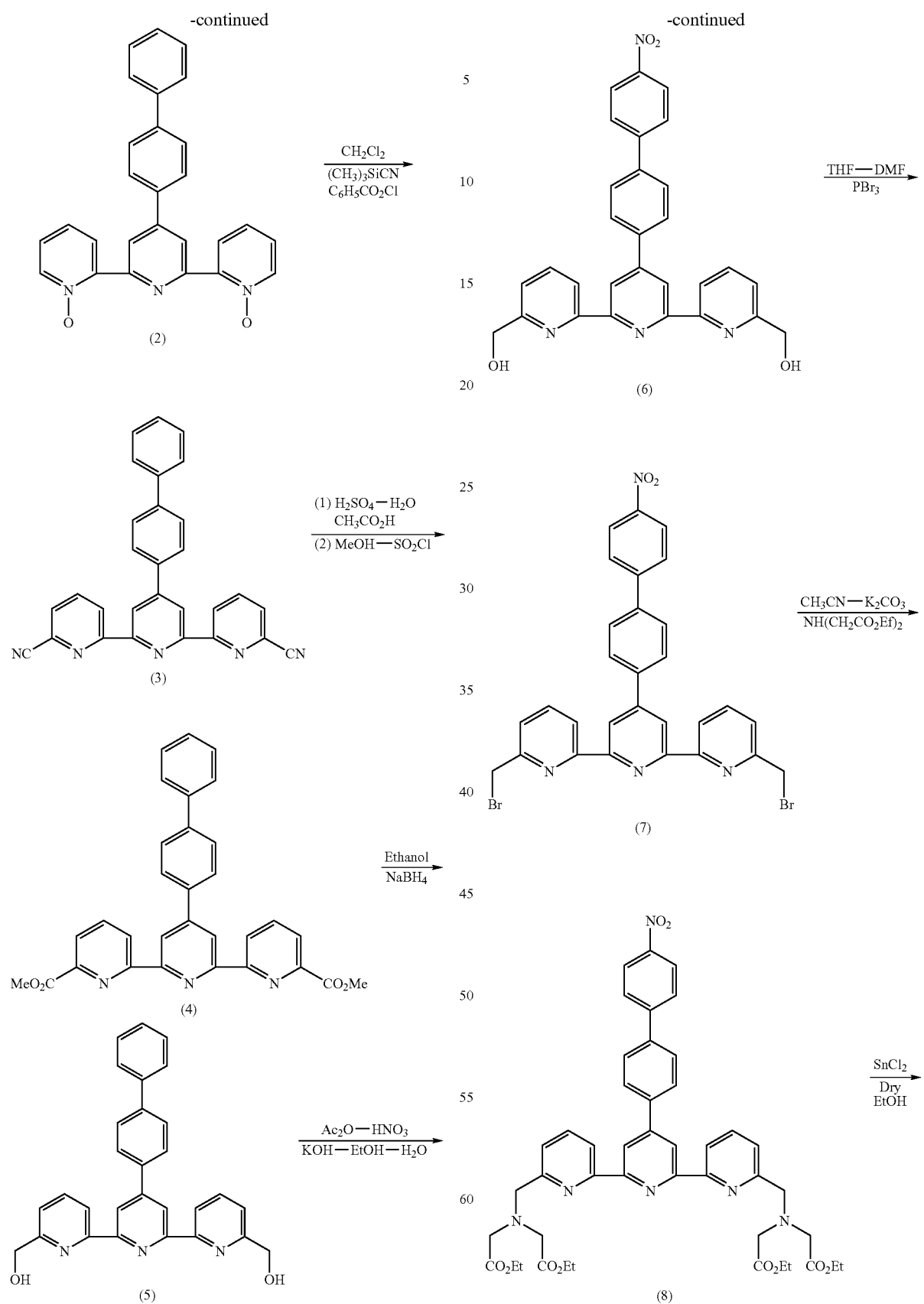

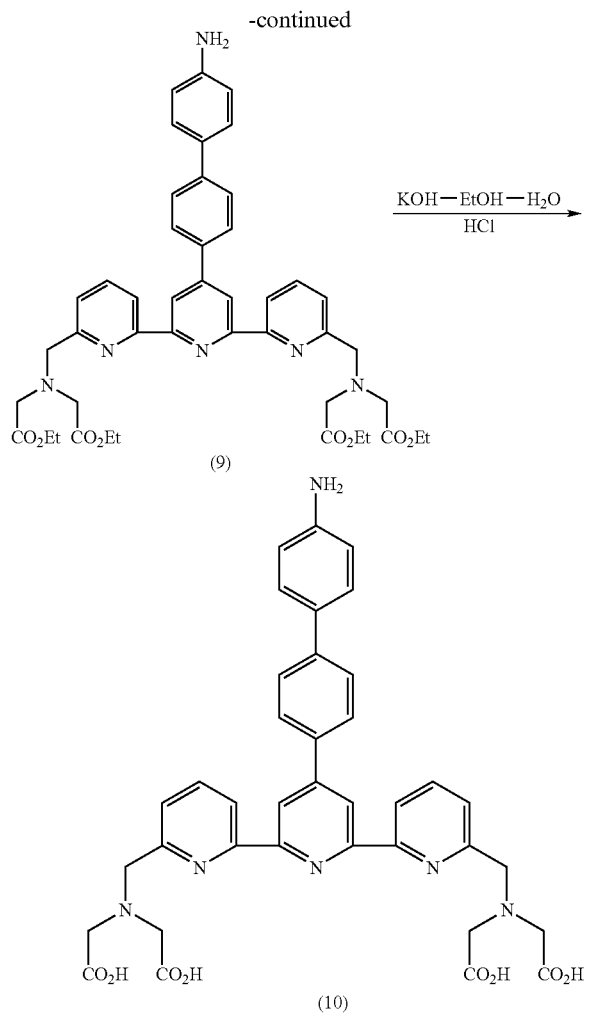

Synthesis of Compound Represented by the General Formula [1-1], ([4'-(4''''-amino-biphenyl-4'''-yl)-2,2': 6',2''-terpyridine-6,6''-diyl)bis(methylene-nitrile)] tetrakis(acetate) (Abbreviated as ATBTA)

(1) Synthesis of 4'-(biphenyl-4'''-yl)-2,2':6',2''-terpyridine [the Compound (1) in the Above-Mentioned Reaction Scheme]

N-[2-(pyrido-2'-yl)-2-oxoethyl]pyridinium iodide (16.3 g, 50 mmol), (E)-3-(biphenyl-4''-yl)-1-(pyrido-2'-yl)-2-propenone (14.26 g, 50 mmol) and ammonium acetate (23.1 g) were added to 500 ml of dried methanol, then the solution was refluxed for 24 hours while stirring. The reaction solution was cooled and a precipitate was obtained by filtration. After the precipitate was washed thoroughly with chilled methanol, recrystallized from acetonitrile, thus the compound (1) was obtained. The yield after vacuum drying was 49.3%.

Results of elementary analysis ($C_{27}H_{19}N_3$):

Calculated value (%), C=84.13; H=4.97; N=10.90. Measured value (%), C=84.01; H=4.82; N=10.88.

Furthermore, the product was confirmed to be the target compound by $^1$H NMR.

$^1$H NMR (CDCl$_3$): δ 8.80 (s, 2H), 8.75 (d, J=4.6 Hz, 2H), 8.69 (d, J=7.8 Hz, 2H), 8.01 (d, J=8.6 Hz, 2H), 7.89 (t, J=7.6 Hz, 2H), 7.75 (d, J=8.2 Hz, 2H), 7.68 (d, J=6.9 Hz, 2H), 7.48 (t, J=6.9 Hz, 2H), 7.41-7.33 (m, 3H).

(2) Synthesis of 4'-(biphenyl-4'''-yl)-2,2':6',2''-terpyridine-1,1''-dioxide [the Compound (2) in the Above-Mentioned Reaction Scheme]

The compound (1) in the above-mentioned reaction scheme (19.27 g, 50 mmol) was dissolved in 700 ml of CH$_2$Cl$_2$, and 50 g of 3-chloroperoxybenzoic acid was added, then stirred for 20 hours at room temperature. The reaction solution was washed with 10% Na$_2$CO$_3$ aqueous solution (3×300 ml), and the organic phase was dried with Na$_2$SO$_4$, then the solvent was removed under reduced pressure. The product was dissolved in 300 ml of methanol, and a trace amount of insoluble substances was removed by filtration, then the solvent was removed under reduced pressure. The product was washed well with acetonitrile and vacuum dried, thus the compound (2) was obtained. The yield was 91.4%. The product was confirmed to be the target compound by $^1$H NMR.

$^1$H NMR (CDCl$_3$): δ 9.29 (s, 2H), 8.38 (d, J=6.6 Hz, 2H), 8.25 (d, J=8.2 Hz, 2H), 7.94 (d, J=8.6 Hz, 2H), 7.72 (d, J=8.6 Hz, 2H), 7.66 (d, J=6.9 Hz, 2H), 7.50-7.43 (m, 2H), 7.41-7.29 (m, 5H).

(3) Synthesis of 4'-(biphenyl-4'''-yl)-2,2':6',2''-terpyridine-6,6''-dicarbonitrile [the Compound (3) in the Above-Mentioned Reaction Scheme]

To 450 ml of CH$_2$Cl$_2$, 25 mmol of the compound (2) in the above-mentioned reaction scheme (15.65 g, 37.5 mmol) and (CH$_3$)$_3$SiCN (37.2 g, 375 mmol) were added and stirred for 20 minutes at room temperature. Then, 150 mmol of benzoyl chloride was added dropwise thereto little by little over the period of about 20 minutes. After the reaction solution was stirred for 24 hours at room temperature, half of the solvent was removed under reduced pressure. To the remaining solution, 600 ml of 10% K$_2$CO$_3$ aqueous solution was added, stirred for 1 hour at room temperature, and a precipitate was obtained by filtration. Subsequently, the precipitate was washed thoroughly with water, further washed with chilled CH$_2$Cl$_2$, then vacuum dried, thus the compound (3) was obtained. The yield was 80.8%. The product was confirmed to be the target compound by $^1$H NMR.

$^1$H NMR (DMSO-d$_6$): δ 8.99 (d, J=7.6 Hz, 2H), 8.75 (s, 2H), 8.31 (t, J=7.9 Hz, 2H), 8.20 (d, J=7.6 Hz, 2H), 8.10 (d, J=7.6 Hz, 2H), 7.92 (d, J=8.2 Hz, 2H), 7.78 (d, J=7.6 Hz, 2H), 7.54-7.42 (m, 3H).

(4) Synthesis of 4'-(biphenyl-4'''-yl)-2,2':6',2''-terpyridine-6,6''-dicarboxylate dimethyl [the Compound (4) in the Above-Mentioned Reaction Scheme]

To a mixed solvent of H$_2$SO$_4$ (90 ml), CH$_3$COOH (90 ml) and H$_2$O (20 ml), 8.71 g (20 mmol) of the compound (3) in the above-mentioned reaction scheme was added, and stirred for 24 hours at 90 to 100° C. The reaction solution was added to 800 g of ice, and stirred, then a precipitate was obtained by filtration. The precipitate was washed thoroughly with water and ethanol, then vacuum dried, thus 9.13 g of a hydrolysate was obtained.

To 600 ml of dried methanol, which had been cooled with ice-water, 24 g of thionyl chloride, SOCl$_2$, was added, and stirred for 15 minutes. Then, 9.13 g of the hydrolysate obtained above was added thereto, and the solution was refluxed for 24 hours while stirring. The solvent was removed under reduced pressure, and the product was dissolved in 1000 ml of chloroform, $CHCl_3$. The organic layer was washed thoroughly with 15% $NaHCO_3$ aqueous solution, then dried with $Na_2SO_4$. The solvent was removed under reduced pressure, and the product was purified with a silica gel column (developing solvent: $CH_2Cl_2$—$CH_3OH$=99:1 w/w). The product was recrystallized from toluene, thus the compound (4) was obtained. The yield was 48.5%.

Results of elementary analysis ($C_{31}H_{23}N_3O_4$):

Calculated value (%), C=74.24; H=4.62; N=8.38. Measured value (%), C=74.15; H=4.55; N=8.38.

Furthermore, the product was confirmed to be the target compound by $^1H$ NMR.

$^1H$ NMR ($CDCl_3$): δ 8.88 (s, 2H), 8.86 (d, J=7.9 Hz, 2H), 8.20 (d, J=7.6 Hz, 2H), 8.06 (d, J=7.9 Hz, 2H), 8.00 (d, J=7.2 Hz, 2H), 7.78 (d, J=6.6 Hz, 2H), 7.70 (d, J=6.9, 2H), 7.52-7.30 (m, 3H), 4.07 (s, 6H)

(5) Synthesis of 4'-(biphenyl-4'''-yl)-2,2':6',2"-terpyridine-6,6"-dihydroxymethyl [Compound (5) in the Above-Mentioned Reaction Scheme]

To 400 ml of dried ethanol, the compound (4) in the above-mentioned reaction scheme (7.02 g, 14 mmol) and 3.02 g of $NaBH_4$ were added, stirred for 3 hours at room temperature, then the solution was refluxed for 1 hour. The solvent was removed under reduced pressure, and the product was added to 200 ml of saturated $NaHCO_3$ aqueous solution, and heated until it boiled while stirring. After the solution was cooled, a precipitate was obtained by filtration. The precipitate was washed thoroughly with water and vacuum dried, thus the compound (5) was obtained. The yield was 92.0%. The product was confirmed to be the target compound by $^1H$ NMR.

$^1H$ NMR (DMSO-$d_6$): δ 8.75 (s, 2H), 8.55 (d, J=7.9 Hz., 2H), 8.07-8.00 (m, 4H), 7.92 (d, J=8.2 Hz, 2H), 7.78 (d, J=7.2 Hz, 2H), 7.61 (d, J=7.9 Hz, 2H), 7.57-7.50 (m, 2H), 7.46-7.40 (m, 1H), 5.57 (t, J=5.9 Hz, 2H), 4.74 (d, J=4.6 Hz, 4H).

(6) Synthesis of 4'-(4''''-nitro-biphenyl-4'''-yl)-2,2':6', 2"-terpyridine-6,6"-dihydroxymethyl [Compound (6) in the Above-Mentioned Reaction Scheme]

The compound (5) in the above-mentioned reaction scheme (1.78 g, 4 mmol) was added to 30 ml of acetic anhydride, stirred for 15 hours at 60° C. The solvent was removed under reduced pressure, and 20 ml of acetic anhydride was added to the product. Then, a solution of 20 ml of acetic acid and 3 ml of fuming nitric acid was added dropwise thereto while the outside was cooled with ice-water. The solution was stirred for 2 hours while the outside was cooled with ice-water, and further stirred for 24 hours at room temperature. The reaction solution was added to 250 ml of water, stirred for 1 hour, and extracted with $CHCl_3$ (3×100 ml). The $CHCl_3$ solution was washed with 5% $NaHCO_3$ aqueous solution, and dried with $Na_2SO_4$, then the solvent was removed under reduced pressure. To the product, 150 ml of ethanol, 10 g of KOH and 15 ml of water were added and stirred for 36 hours at room temperature. To the reaction solution, 30 ml of water was added, and the precipitate was collected by centrifugation. The precipitate was vacuum dried for 5 hours, and washed thoroughly with water, then vacuum dried again, thus the compound (6) was obtained. The yield was 90.7%. The product was confirmed to be a mixture of the target compound and 4'-(2''''-nitro-biphenyl-4'''-yl)-2,2':6',2"-terpyridine-6,6"-dihydroxymethyl by $^1H$ NMR.

$^1H$ NMR (DMSO-$d_6$): δ8.81-8.79 (m, 2H), 8.61 (d, J=7.9 Hz, 2H), 8.37 (d, J=7.2 Hz, 1H), 8.17-8.03 (m, 6H), 7.88-7.80 (m, 1H), 7.75-7.58 (m, 4H), 4.78 (s, 4H).

(7) Synthesis of 4'-(4''''-nitro-biphenyl-4'''-yl)-2,2':6', 2"-terpyridine-6,6"-dibromomethyl [Compound (7) in the Above-Mentioned Reaction Scheme]

The compound (6) in the above-mentioned reaction scheme (1.78 g, 3.63 mmol) was dissolved in a mixed solvent of THF (200 ml) and DMF (80 ml), and 3.52 g of $PBr_3$ was added, then the solution was refluxed for 6 hours while stirring. After the solvent was removed under reduced pressure, 300 ml of $CHCl_3$ was added to the product, and the organic layer was washed with saturated $Na_2SO_4$ aqueous solution (4×200 ml), and further washed with 200 ml of 10% $NaHCO_3$ aqueous solution. The organic phase was dried with $Na_2SO_4$, and the solvent was removed under reduced pressure, then the product was purified with a silica gel column (developing solvent: $CH_2Cl_2$—$CH_3OH$=99.5:0.5 v/v). The solvent was removed under reduced pressure, and the residue was vacuum dried, thus the compound (7) was obtained. The yield was 56.3%.

Results of elementary analysis ($C_{29}H_{20}Br_2N_4O_2$):

Calculated value (%), C=56.52; H=3.27; N=9.09. Measured value (%), C=56.64; H=3.32; N=9.10.

Results of mass spectrometry (FAB-MS) m/e, 617.3 (M+H$^+$), 571.3 (M−NO$_2$)

Furthermore, the product was confirmed to be a mixture of the target compound and 4'-(2''''-nitro-biphenyl-4'''-yl)-2,2':6', 2"-terpyridine-6,6"-dibromomethyl by $^1H$ NMR.

$^1H$ NMR ($CDCl_3$): δ 8.70 (s, 1H), 8.69 (s, 1H), 8.57 (d, J=7.9 Hz, 2H), 8.33 (d, J=8.8 Hz, 1H), 8.10-8.00 (m, 6H), 7.95 (d, J=8.2 Hz, 1H), 7.70-7.55 (m, 4H), 4.84 (s, 4H).

(8) Synthesis of tetraethyl N,N,N',N'-[4'-(4''''-nitro-biphenyl-4'''-yl)-2,2':6',2"-terpyridine-6,6"-diyl)bis (methylenenitrilo)]tetrakis(acetate) [Compound (8) in the Above-Mentioned Reaction Scheme]

The compound (7) in the above-mentioned reaction scheme (1.22 g, 1.98 mmol) was dissolved in a mixed solvent of 250 ml of $CH_3CN$ and 50 ml of THF, and 4.1 mmol of diethyliminodiacetate and 20 mmol of $K_2CO_3$ were added, then the solution was refluxed for 24 hours while stirring. The insoluble substances were removed by filtration, and the solvent was removed under reduced pressure. Then, 250 ml of $CHCl_3$ was added to the product, and the $CHCl_3$ solution was washed with saturated $Na_2SO_4$ aqueous solution (2×200 ml). The organic phase was dried with $Na_2SO_4$, and the solvent was removed under reduced pressure. Then the oily product was purified with a silica gel column (developing solvent: $CH_3COOEt$). The solvent was removed under reduced pressure, and the residue was vacuum dried, thus the compound (8) was obtained. The yield was 46.1%. The product was confirmed to be a mixture of the target compound and 4'-(2''''-nitro-biphenyl-4'''-yl)-2,2':6',2"-terpyridine-6,6-diyl)bis (methylenenitrilo)]tetrakis(acetate) by $^1H$ NMR.

$^1H$ NMR ($CDCl_3$): δ 8.77 (s, 2H), 8.57 (d, J=7.9 Hz, 2H), 8.36 (d, J=8.6 Hz, 1H), 8.05 (d, J=7.9 Hz, 1H), 7.98-7.79 (m, 6H), 7.66 (d, J=7.6 Hz, 2H), 7.57-7.42 (m, 2H), 4.21 (s, 4H), 4.17 (q, J=7.3 Hz, 8H), 3.71 (s, 8H), 1.24 (t, J=7.3 Hz, 12H).

(9) Synthesis of tetraethyl N,N,N',N'-[4'-(4''''-amino-biphenyl-4'''-yl)-2,2':6',2''-terpyridine-6,6''-diyl)bis(methylenenitrilo)]tetrakis(acetate) [Compound (9) in the Above-Mentioned Reaction Scheme]

The compound (8) in the above-mentioned reaction scheme (0.76 g, 0.91 mmol) was dissolved in 60 ml of EtOH, and $SnCl_2 2H_2O$ (5.7 mmol, 1.25 g) was added and stirred for 1 hour at 70 to 80° C. After it was cooled to room temperature, poured into a solution of $H_2O$ (120 ml) and DTPA (7.85 g), which had been cooled in an ice water bath, and stirred. Then, 20 ml of saturated $NaHCO_3$ aqueous solution was added to the solution, stirred for 30 minutes at room temperature. Then, the aqueous solution was extracted with $CHCl_3$ (4×100 ml), and the organic phase was dried with $Na_2SO_4$. The solvent was removed under reduced pressure, and the product was purified with a silica gel column (developing solvent: $CH_3COOEt$-$CH_3OH$=98:2 v/v). The solvent was removed under reduced pressure, then the residue was vacuum dried, thus the compound (9) was obtained. The yield was 79.2%. The product was confirmed to be the target compound by $^1H$ NMR.

$^1H$ NMR ($CDCl_3$): δ 8.76 (s, 2H), 8.55 (d, J=7.3 Hz, 2H), 8.00-7.84 (m, 4H), 7.72-7.62 (m, 4H), 7.51 (d, J=8.6 Hz, 2H), 6.81 (d, J=8.6 Hz, 2H), 4.21 (s, 4H), 4.17 (q, J=7.3 Hz, 8H), 3.71 (s, 8H), 1.24 (t, J=7.3 Hz, 12H).

(10) Synthesis of [4'-(4''''-amino-biphenyl-4'''-yl)-2,2':6',2''-terpyridine-6,6''-diyl)bis(methylene-nitrilo)]tetrakis(acetate) [ATBTA, Compound (10) in the Above-Mentioned Reaction Scheme]

The compound (9) in the above-mentioned reaction scheme (0.72 mmol, 580 mg) was dissolved in a solution of EtOH (100 ml), $H_2O$ (5 ml) and KOH (2.2 g) and stirred for 20 hours at room temperature, then the solvent was removed under reduced pressure. After the product was dissolved in 100 ml of water, a hydrochloric acid aqueous solution, which had been diluted to 10-fold, was added dropwise while stirring little by little to adjust the pH of the solution to about 1. After the solution was stirred for 3 hours at room temperature, a precipitate was collected by centrifugation. The precipitate was washed thoroughly with a hydrochloric acid aqueous solution, which had been diluted to 100-fold and vacuum dried, thus the compound (10) was obtained. The yield was 65.9%.

Results of elementary analysis (ATBTA.$3HCl.4H_2O$, $C_{37}H_{45}N_6O_{12}Cl_3$):
Calculated value (%), C=50.95; H=5.20; N=9.64. Measured value (%), C=51.05; H=5.36; N=9.65.

Furthermore, the product was confirmed to be the target compound by $^1H$ NMR.

$^1H$ NMR (DMSO-$d_6$): δ 8.89 (s, 2H), 8.75 (d, J=7.9 Hz, 2H), 8.23-8.05 (m, 4H), 7.96-7.80 (m, 2H), 7.75 (d, J=7.6 Hz, 2H), 7.60-7.45 (m, 4H), 4.68 (s, 4H), 4.24 (s, 8H).

The above-mentioned ATBTA.$3HCl.4H_2O$ was further washed thoroughly with purified water and acetonitrile, then vacuum dried, thus ATBTA was obtained.

Results of elementary analysis ($C_{37}H_{34}N_6O_8$)
Calculated value (%), C=64.34; H=4.96; N=12.17. Measured value (%), C=63.89; H=5.11; N=12.14.

Furthermore, the product was confirmed to be the target compound by $^1H$ NMR.

$^1H$ NMR (DMSO-$d_6$): δ 8.75 (s, 2H), 8.56 (d, J=7.9 Hz, 2H), 8.06-8.00 (m, 4H), 7.93-7.71 (m, 2H), 7.66 (d, J=7.6 Hz, 2H), 7.60-7.40 (m, 4H), 4.13 (s, 4H), 3.59 (s, 8H).

Example 11

Synthesis of Complex of ATBTA and Europium

ATBTA.$3HCl.4H_2O$ produced in the above-mentioned Example 10 (0.2 mmol, 164.4 mg) was added to 4.0 ml of water, and the pH of the solution was adjusted to 6.5 with solid $NaHCO_3$. Then, a solution of $EuCl_3.6H_2O$ (0.22 mmol, 80.6 mg) and $H_2O$ (1.5 ml) was added and stirred for 1.5 hours while the pH of the solution was maintained at 6.5 with $NaHCO_3$. After the pH of the reaction solution was adjusted to 8.5 with 1 M NaOH solution, the precipitate was removed by filtration and the filtrate was recovered. To the filtrate, 80 ml of acetone was added to deposit a complex. The complex was collected by centrifugation, and washed thoroughly with acetone, then vacuum dried, thus a complex of ATBTA and europium was obtained. The yield was 180 mg.

Results of elementary analysis [Na[$C_{37}H_3ON_6O_8Eu$].($NaHCO_3$)$_3$.(NaCl)$_2$.(H$_2$O)$_4$]:
Calculated value (%), C=36.88; H=3.17; N=6.45. Measured value (%), C=36.74; H=3.09; N=6.26.

Example 12

Introduction of Amino Reaction Active Substituent into ATBTA-$Eu_{3+}$ Complex

The ATBTA-$Eu^{3+}$ complex produced by the method described in Example 11 was dissolved in 3.0 ml of 0.1 M sodium acetate buffer solution (pH 4.9), and 2,4,6-trichloro-1,3,5-triazene (0.2 mmol, 36 mg) was added, then 2 ml of acetone and 2 ml of water were added while stirring. After the solution was stirred for 30 minutes at room temperature, 120 ml of acetone was added thereto to deposit a complex. The precipitate was collected by centrifugation, washed thoroughly with acetone, then vacuum dried, thus a complex having an active substituent was obtained. The yield was 139 mg.

Example 13

Fluorescence Characteristics of ATBTA-$Eu^{3+}$ Complex Having Active Substituent Fluorescence spectra of the ATBTA-$Eu^{3+}$ complex (1.5× $10^{-6}$ M) having an active substituent produced in Example 12 were measured in 0.05 M borate buffer solution (pH 9.1).

Figure 4:
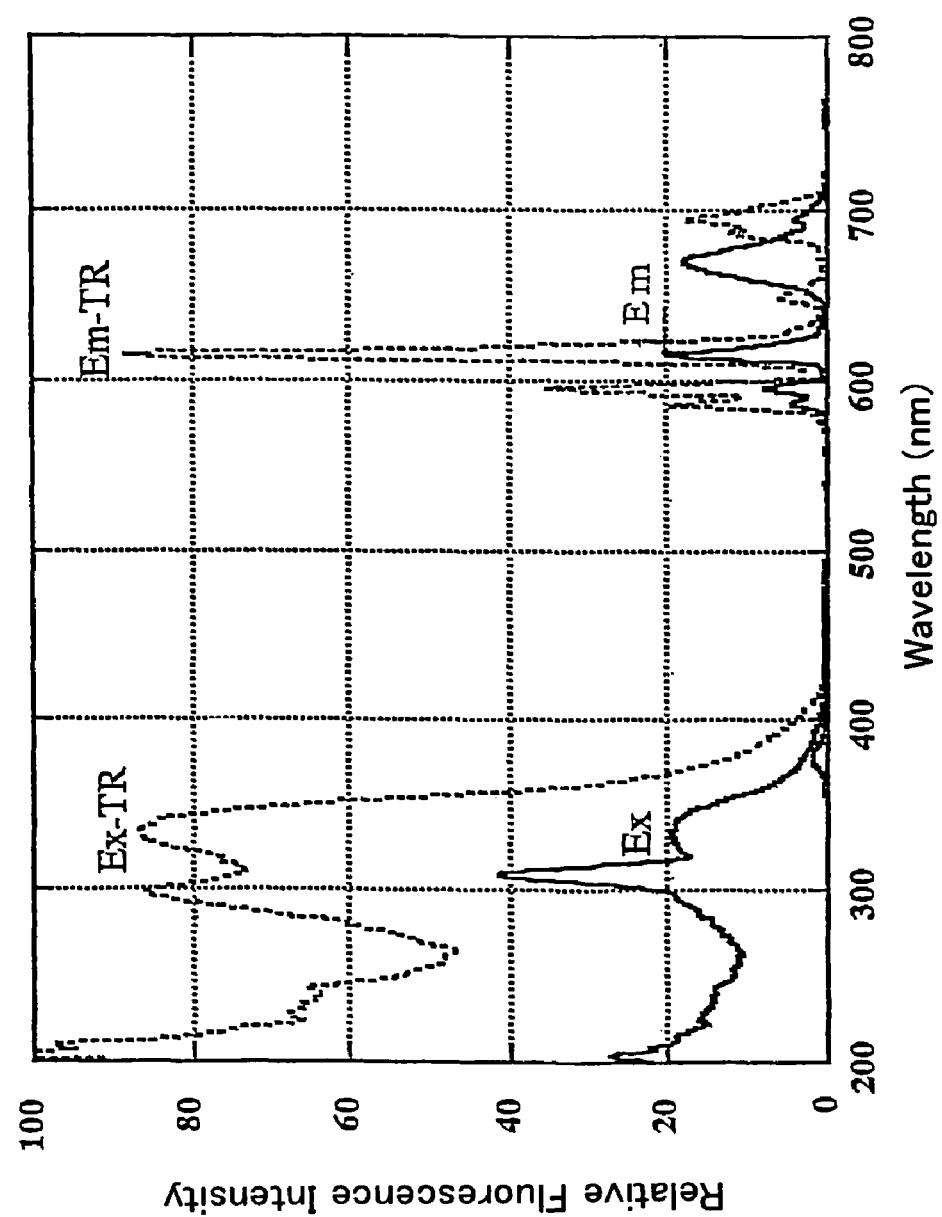
FIG. 4 is a diagram showing the fluorescence spectra of the ATBTA-Eu$^{3+}$ complex having an active substituent of the present invention. [ATBTA-Eu$^{3+}$]=1.5×10$^{-6}$ M in 0.05 M borate buffer solution (pH 9.1).

The measurement results are shown in FIG. 4. The vertical axis of FIG. 4 shows the relative fluorescence intensity, the horizontal axis shows the wavelength (nm). In FIG. 4, Ex indicates the excitation spectrum, Em indicates the luminescence spectrum, Ex-TR indicates the time-resolved excitation spectrum and Em-TR indicates the time-resolved luminescence spectrum.

The fluorescence characteristics of the complex were as follows: the absorption maximum wavelength was 335 nm, the molar extinction coefficient was $3.11×10^4$ $M^{-1}$ $cm^{-1}$, the fluorescence maximum wavelength was 616 nm, the fluorescence quantum yield was 0.091 and the fluorescence lifetime was 1.02 ms.

Example 14

Production of Compound Represented by General Formula [2-1]

A compound represented by the general formula [2-1] in which R is a biphenyl-4-yl group was produced according to the reaction scheme shown below.

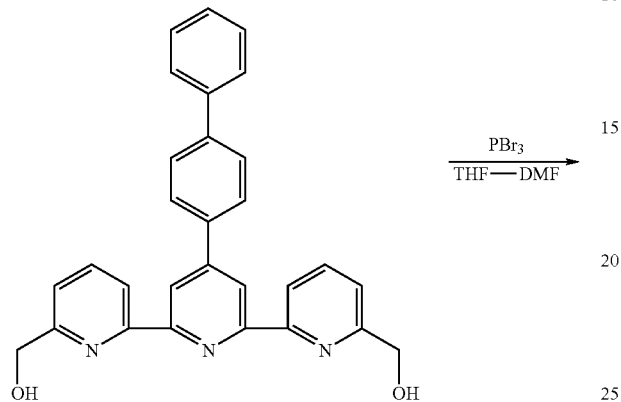

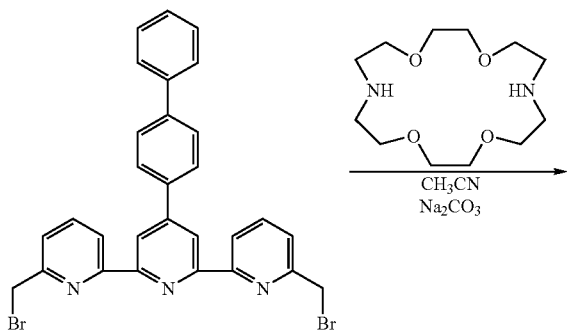

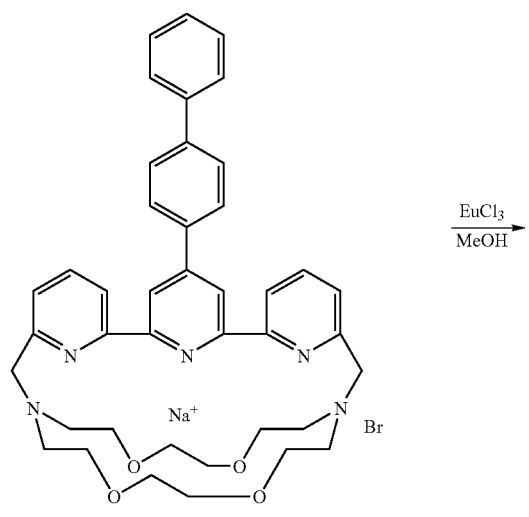

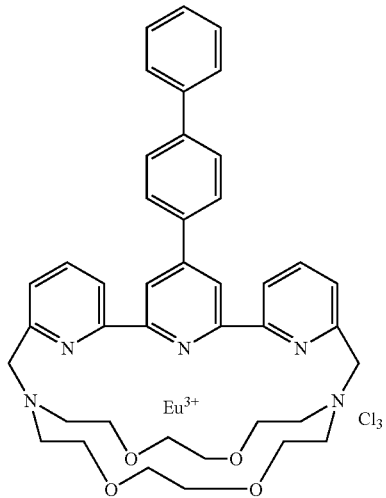

Synthesis of compound represented by the general formula [2-1]

(1) Synthesis of 4'-(biphenyl-4'''-yl)-2,2':6',2''-terpyridine-6,6''-dibromomethyl 4'-(biphenyl-4'''-yl)-2,2':6',2''-terpyridine-6,6''-dihydroxymethyl (4.46 g, 10 mmol) was dissolved in a mixed solvent of THF (400 ml) and DMF (150 ml), then 8.1 g of $PBr_3$ was added, then the solution was refluxed for 16 hours while stirring. After the solvent was removed under reduced pressure, 400 ml of $CHCl_3$ was added to the product. Then, the organic layer was washed with saturated $Na_2SO_4$ aqueous solution (4×200 ml), and further washed with 200 ml of 10% $NaHCO_3$ aqueous solution. The organic phase was dried with $Na_2SO_4$, and the solvent was removed under reduced pressure, then the product was purified with a silica gel column (developing solvent: $CH_2Cl_2$—$CH_3OH$=99:1 v/v). The solvent was removed under reduced pressure, and the residue was vacuum dried, thus 4'-(biphenyl-4'''-yl)-2,2':6',2''-terpyridine-6,6''-dibromomethyl was obtained. The yield was 80.6%.

Results of elementary analysis ($C_{29}H_{21}Br_2N_3$):

Calculated value (%), C=60.97; H=3.70; N=7.35. Measured value (%), C=60.94; H=3.54; N=7.33.

Furthermore, the product was confirmed to be the target compound by $^1H$ NMR.

$^1H$ NMR ($CDCl_3$): δ 8.81 (s, 2H), 8.59 (d, J=7.9 Hz, 2H), 7.99 (d, J=7.9 Hz, 2H), 7.89 (t, J=7.6 Hz, 2H), 7.79 (d, J=7.6 Hz, 2H), 7.69 (d, J=7.3 Hz, 2H), 7.55-7.47 (m, 4H), 7.50-7.35 (m, 1H).

(2) Synthesis of 4-(biphenyl-4'''-yl)-2,2':6',2''-terpyridine-6,6''-diyl)bis(methylenenitrilo)]-N:N',N:N'-(3,6-dioxa-triethylene)

4'-(biphenyl-4'''-yl)-2,2':6',2''-terpyridine-6,6''-dibromomethyl (0.50 mmol, 0.29 g) was dissolved in 250 ml of $CH_3CN$, and 0.50 mmol of 4,13-diaza-18-crown 6-ether and 5.0 mmol of $Na_2CO_3$ were added, then the solution was refluxed for 24 hours while stirring. The insoluble substances were removed by filtration, and the solvent was removed under reduced pressure. The product was purified with an aluminum column (developing solvent: $CHCl_3$—$CH_3OH$=97:3 w/w). The yield was 51%. The product was confirmed to be a complex of NaBr with the target compound (1:1, M.W.=694.7) by FAB-MS. Furthermore, the target compound was confirmed by $^1H$ NMR.

$^1H$ NMR ($CDCl_3$): δ 8.55 (s, 2H), 8.39 (d, J=7.9 Hz, 2H), 8.15-8.09 (m, 4H), 7.92 (d, J=8.6 Hz, 2H), 7.77 (d, J=8.2 Hz, 2H), 7.56-7.49 (m, 4H), 7.47-7.40 (m, 1H), 4.15 (s, 4H), 3.70-3.40 (m, 16H); 3.00-2.55 (m, 8H).

Example 15

Synthesis of Complex of Europium and [(4-(biphenyl-4'''-yl)-2,2':6',2''-terpyridine-6,6''-diyl) bis(methylenenitrilo)]-N:N',N:N'-(3,6-dioxa-triethylene)

The complex of 4-(biphenyl-4'''-yl)-2,2':6',2''-terpyridine-6,6''-diyl)bis(methylenenitrilo)]-N:N',N:N'-(3,6-dioxa-triethylene)-NaBr (0.70 mmol, 0.54 g) was dissolved in 160 ml of anhydrous methanol, and 1 mmol of $EuCl_3.6H_2O$ was added, then the solution was refluxed for 24 hours while stirring. The reaction solution was cooled to room temperature, and 80 ml of ether was added to the reaction solution to deposit a complex. The precipitate was collected by centrifugation and vacuum dried, thus the target compound was obtained. The yield was 62%.

The product was confirmed to be the target compound by FAB-MS.

m/e: 894.6 [M+Eu+2Cl]

859.7 [M+Eu+Cl]

412.4 [Crown+Eu+Cl]

Example 16

Assay for Prostate-Specific Antigen (Abbreviated as PSA) in Human Serum by Time-Resolved Fluoroimmunoassay Using Novel Labeling Agent Having an Amino Reaction Active Substituent, {{4'-[4''''-(4,6-dichloro-1,3,5-triazene-2-yl)amino-biphenyl-4'''-yl]-2,2':6',2''-terpyridine-6,6''-diyl}bis(methylenenitrile) tetrakis (acetate)}europium (III) (Abbreviated as DTBTA-Eu$^{3+}$)

1. Labeling of Streptavidin (Abbreviated as SA) using DTBTA-Eu$^{3+}$

After 2 mg of SA was dissolved in 1.5 ml of 0.1 M sodium carbonate buffer solution (pH 9.1), 2.8 mg of DTBTA-Eu$^{3+}$ dissolved in 0.7 ml of 0.1 M sodium carbonate buffer solution (pH 9.1) was added, and continuously stirred for 3 hours at room temperature. The unreacted labeling reagent was separated from the labeled protein by gel filtration of the reaction solution (using a Sephadex G-50 column (1.0×40 cm), and developed with 0.05 M $NH_4HCO_3$ solution). By measuring the absorbance of the labeled SA solution at 335 nm, the concentration of DTBTA-Eu$^{3+}$ in the labeled SA solution was calculated (based on the assumption that the molar extinction coefficient of labeling agent does not change before and after labeling), and the labeling ratio of the labeled SA was calculated, whereby a solution of SA(DTBTA-Eu$^{3+}$)$_{26}$ was obtained. To the solution of SA(DTBTA-Eu$^{3+}$)$_{26}$, 15 mg of $NaN_3$ was added as an antiseptic and 30 mg of BSA was added to prevent the labeled protein from adhering to the container. Then, the solution was stored at −20° C. When the solution is used for a time-resolved fluoroimmunoassay, use it after diluting to 400-fold with 0.05M Tris-HCl buffer solution (pH7.8) containing 0.2% BSA, 0.9% NaCl and 0.1% $NaN_3$.

2. Labeling of SA-BSA Conjugate Using DTBTA-Eu$^{3+}$

After 1 mg of SA and 1 mg of BSA were dissolved in 1.0 ml of 0.1 M sodium phosphate buffer solution (pH 7.1), 0.03 ml of 1% glutaraldehyde was added, stirred, and let stand at 4° C. for 24 hours. Thereto was added 2 mg of $NaBH_4$, stirred, and let stand for 2 hours at room temperature. The obtained solution was dialyzed twice against 3 L of 0.9% NaCl solution at 4° C. (for 24 hours each). Then, 0.6 ml of 0.5M sodium carbonate buffer solution (pH 9.1) was added, and 1.64 mg of DTBTA-Eu$^{3+}$ dissolved in 0.82 ml of 0.1 M sodium carbonate buffer solution (pH 9.1) was added, then the solution was continuously stirred for 3 hours at room temperature. The unreacted labeling reagent was separated from the labeled protein by gel filtration of the reaction solution. By measuring the absorbance of the labeled SA-BSA solution at 335 nm, the concentration of DTBTA-Eu$^{3+}$ in the labeled SA-BSA solution was calculated, and the labeling ratio of the labeled SA-BSA was calculated, whereby a solution of about SA(BSA)$_{0.9}$(DTBTA-Eu$^{3+}$)$_{42}$ was obtained. To the solution of SA(BSA)$_{0.9}$(DTBTA-Eu$^{3+}$)$_{42}$, 15 mg of $NaN_3$ was added as an antiseptic and 30 mg of BSA was added to prevent the labeled protein from adhering to the container. Then, the solution was stored at −20° C. When the solution is used for a time-resolved fluoroimmunoassay, use it after diluting to 400-fold with 0.05M Tris-HCl buffer solution (pH7.8) containing. 0.2% BSA, 0.9% NaCl and 0.1% $NaN_3$.

3. Labeling of Mouse Anti-Human PSA Monoclonal Antibody Using DTBTA-Eu$^{3+}$

To 0.6 ml of mouse anti-PSA monoclonal antibody (OEM Concepts, 0.5 mg/ml, Clone No: 131-14234) after dialysis, 0.2 ml of 0.5M sodium carbonate buffer solution (pH 9.1) was added, and 0.117 mg of DTBTA-Eu$^{3+}$ dissolved in 0.032 ml of 0.1M sodium carbonate buffer solution (pH 9.1) was added, and continuously stirred for 2.5 hours at room temperature. The unreacted labeling reagent was separated from the labeled protein by gel filtration of the reaction solution. By measuring the absorbance of the labeled antibody solution at 335 nm, the concentration of DTBTA-Eu$^{3+}$ in the labeled antibody solution was calculated, then the labeling ratio of the labeled antibody was calculated, whereby a labeled antibody solution with a labeling ratio of about 20 was obtained. To the solution, 10 mg of $NaN_3$ was added as an antiseptic and 10 mg of BSA (bovine serum albumin) was added to prevent the labeled protein from adhering to the container. Then, the solution was stored at −20° C. When the solution is used for a time-resolved fluoroimmunoassay, use it after diluting to 200-fold with 0.05 M Tris-HCl buffer solution (pH 7.8) containing 0.2% BSA, 0.9% NaCl and 0.1% $NaN_3$.

4. Time-Resolved Fluoroimmunoassay for Human PSA using SA(DTBTA-Eu$^{3+}$)$_{26}$ and SA(BSA)$_{0.9}$(DTBTA-Eu$^{3+}$)$_{42}$ An assay was preformed using a 96-well microtiter plate. Specific operation procedures are as follows.

(1) Preparation of biotinylated antibody: To 0.4 ml (0.5 mg/ml) of a mouse anti-PSA monoclonal antibody solution (OEM Concepts, Clone No: 131-14234) after dialysis, 0.6 ml of purified water, 8.4 mg of $NaHCO_3$ and 2 mg of sulfosuccinimidyl-6-(biotinamido)hexanoate (NHS-LC-Biotin, Pierce Chem. Co.) were added, then the solution was stirred for 1 hour at room temperature, followed by incubating for 24 hours at 4° C. After the reaction solution was dialyzed twice against 3 L of 0.1 M $NaHCO_3$ solution containing 0.25 g of NaN3 at 4° C. for 24 hours each, 10 mg of BSA was added, then the solution was stored at −20° C. until it was used for an immunoassay. When the solution is used for an immunoassay, use it after diluting to 1000-fold with 0.05M Tris-HCl buffer solution (pH 7.8) containing 0.2% BSA, 0.9% NaCl and 0.1% $NaN_3$.

(2) Coating of 96-well microtiter plate: After a mouse anti-human PSA monoclonal antibody (OEM Concepts, Clone No: 131-11214) was diluted to 12.5 μg/ml with a 0.1 M carbonate buffer solution (pH 9.6), a 50 μl aliquot of the solution was dispensed into a 96-well microtiter plate made of transparent polystyrene (FluoroNunc plate) and incubated for 24 hours at 4° C. Subsequently, the plate was washed twice with 0.05 M Tris-HCl buffer solution (pH 7.8) containing 0.05% Tween 20 (Buffer 1), and further washed once with 0.05 M Tris-HCl buffer solution (pH 7.8) (Buffer 2).

(3) Immunoassay for PSA: Into each well of the antibody coated 96-well microtiter plate, a 45 μl aliquot of PSA standard solution (Biogenesis Inc.) was dispensed, and incubated for 2 hours at 37° C. Then, the plate was washed twice with Buffer 1 and once with Buffer 2. Into the respective wells, a 45 μl aliquot of the biotinylated anti-human PSA antibody was dispensed, and incubated for 1 hour at 37° C. Then, the plate was washed twice with Buffer 1 and once with Buffer 2. Into the respective wells, a 45 μl aliquot of the $SA(DTBTA-Eu^{3+})_{26}$ or $SA(BSA)_{0.9}(DTBTA-Eu^{3+})_{42}$ was dispensed, and incubated for 1 hour at 37° C. Then, the plate was washed four times with Buffer 1, and continuously used for a solid phase time-resolved fluorescence assay.

The device for time-resolved fluorescence assay used in this measurement was the DELFIA 1234 time-resolved fluorometer (Wallac), and the measurement conditions were as follows: the excitation wavelength=340 nm, the measurement wavelength=615 nm, the delay time=0.2 ms, the window time=0.4 ms, the cycling time=1.0 ms.

Figure 5:
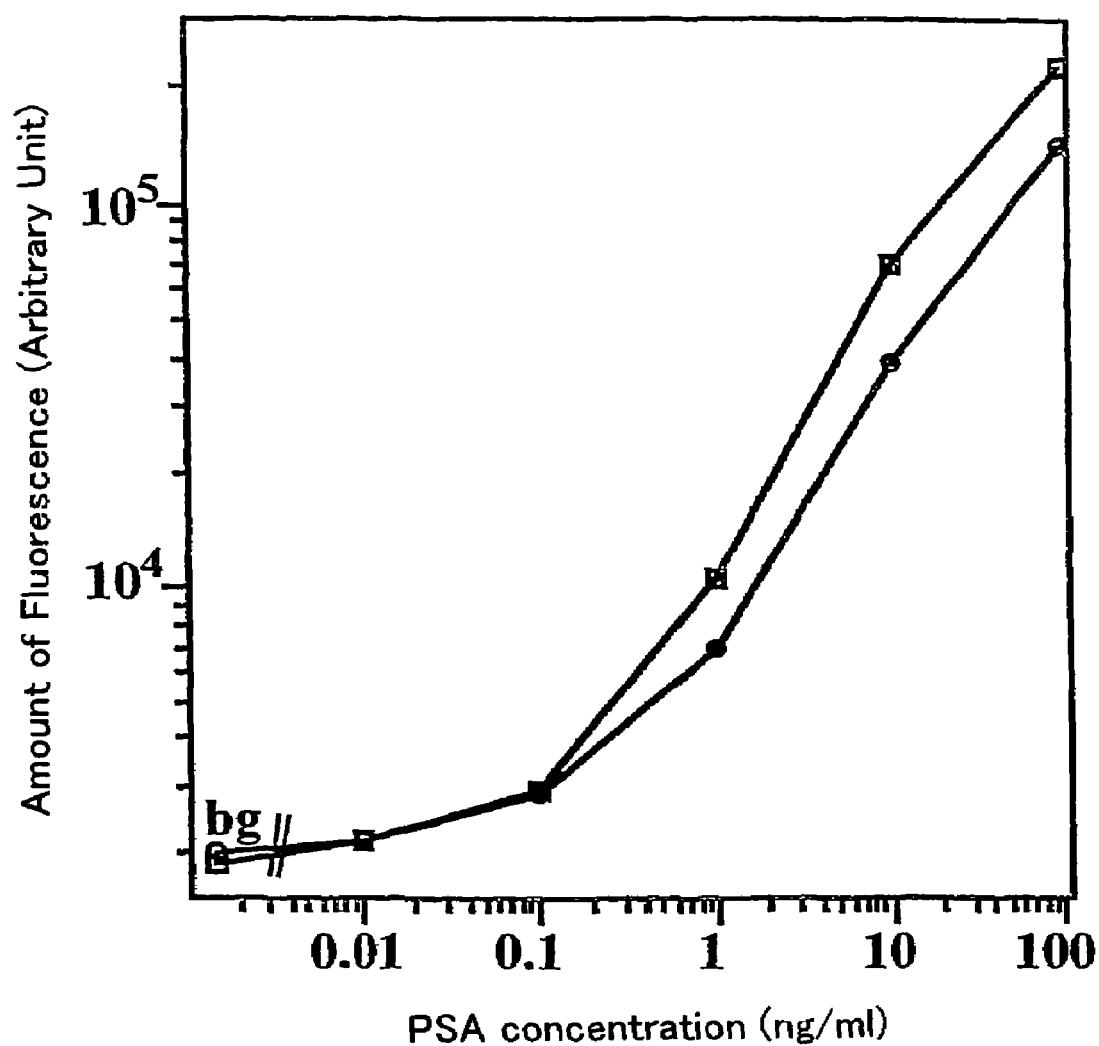
FIG. 5 is a diagram showing the calibration curve of the human PSA assay obtained by the time-resolved fluoroimmunoassay using SA(DTBTA-Eu$^{3+}$)$_{26}$ (□) and SA(BSA)$_{0.9}$ (DTBTA-Eu$^{3+}$)$_{42}$ (○).

The calibration curve obtained by the above immunoassay is shown in FIG. 5. In the case where the background signal+3 SD (standard deviation) was assigned to the detection limit, the detection limit of the method using $SA(DTBTA-Eu^{3+})_{26}$ was 22 pg/ml, and the detection limit of the method using $SA(BSA)_{0.9}(DTBTA-Eu^{3+})$ 42 was 0.8 pg/ml.

5. Time-resolved fluoroimmunoassay for Human PSA using mouse Anti-human PSA monoclonal antibody labeled with $DTBTA-Eu^{3+}$ Into each well of the 96-well microtiter plate coated with a mouse anti-human PSA monoclonal antibody (OEM Concepts, Clone No: 131-11214), a 45 μl aliquot of PSA standard solution was dispensed, and incubated for 2 hours at 37° C. Then, the plate was washed twice with Buffer 1 and once with Buffer 2. Into the respective wells, a 45 μl aliquot of the mouse anti-human PSA monoclonal antibody (OEM Concepts, Clone No: 131-14234) labeled with $DTBTA-Eu^{3+}$ was dispensed, and incubated for 1 hour at 37° C. Then, the plate was washed-four times with Buffer 1, and continuously used for a solid phase time-resolved fluorescence assay. The measurement conditions were the same as above.

Figure 6:
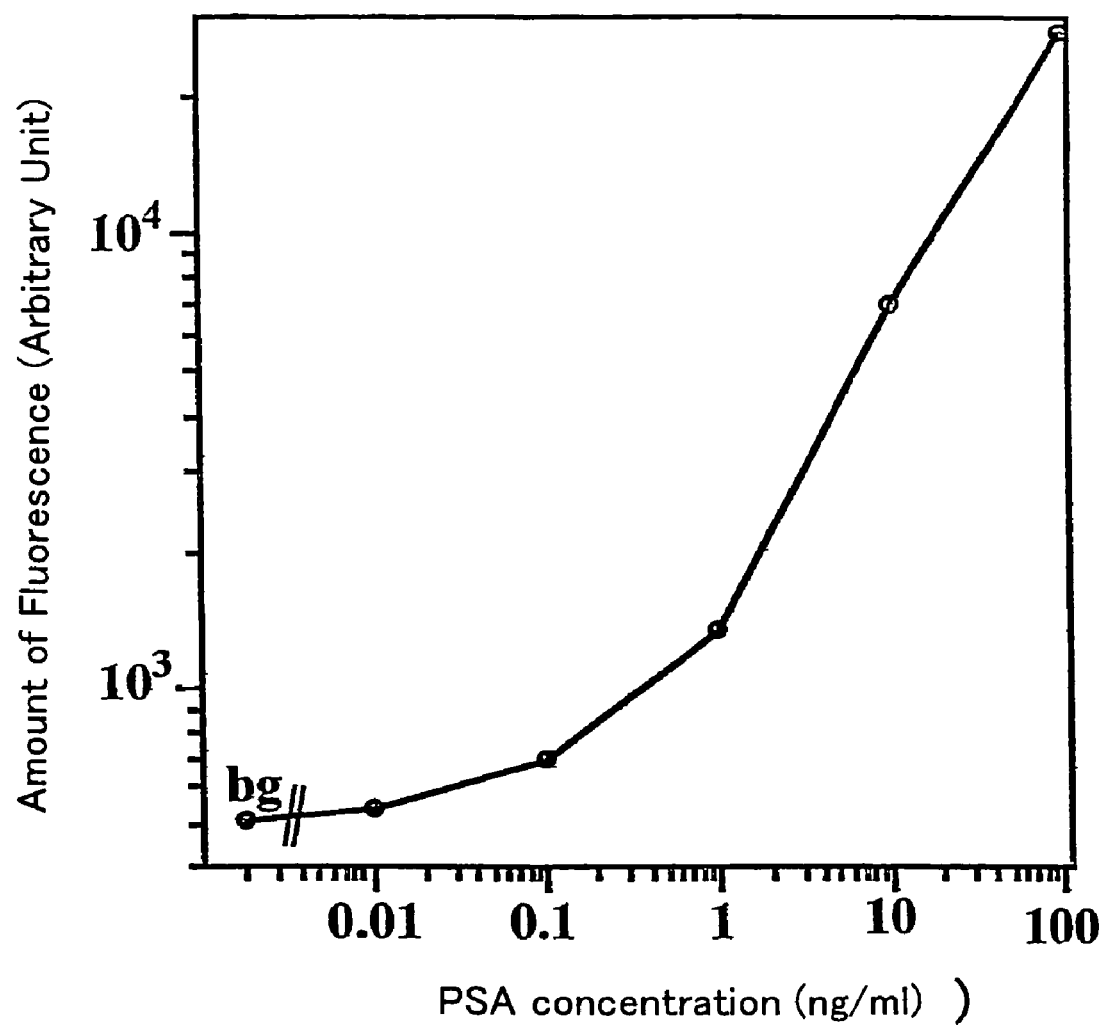
FIG. 6 is a diagram showing the calibration curve of the human PSA assay obtained by the time-resolved fluoroimmunoassay using a mouse anti-human PSA monoclonal antibody labeled with DTBTA-Eu$^{3+}$.

The calibration curve obtained by the above immunoassay is shown in FIG. 6. In the case where the background signal+3 SD (standard deviation) was assigned to the detection limit, the detection limit of this method was 41 pg/ml.

INDUSTRIAL APPLICABILITY

The present invention provides a novel labeling reagent which has a binding group capable of binding to a substance to be labeled (for example, a biological substance or a physiologically active substance or the like) and is capable of easily forming a complex together with a rare earth metal ion. The complex is very stable in an aqueous solution, and has a sufficient fluorescence intensity and a long fluorescence lifetime. Therefore, by using the complex, it becomes possible to directly label an enzyme, a protein, a peptide (oligopeptide or polypeptide), a hormone, a nucleic acid probe, an oligonucleotide or a medicinal substance (including an antibiotic), which has a functional group such as an amino group or a mercapto group, other organic compounds and the like in an aqueous solution.

In addition, the novel labeling reagent according to the present invention forms a very stable labeled composite together with a substance to be labeled (specifically, an enzyme, a protein, a peptide (oligopeptide or polypeptide), a hormone, a nucleic acid probe, an oligonucleotide or a medicinal substance (including an antibiotic), which has an amino group, a mercapto group, or the like, other organic compounds or the like) by forming a covalent bond, thereby enabling to obtain a very stable labeled composite of rare earth fluorescent complex by reacting the labeled composite with a rare earth ion. The labeled composite also has a very long fluorescence lifetime and a strong fluorescence in the same manner, and can be directly applied to a time-resolved fluoroimmunoassay, a DNA hybridization assay or the like.

The invention claimed is:

1. A labeling reagent for fluorescent labeling comprising a compound having a 2,2':6',2"-tripyridine skeleton or a 2,6-dipyrazolopyridine skeleton wherein the labeling reagent comprises the compound having a 2,2':6',2"-tripyridine skeleton represented by the general formula [1]:

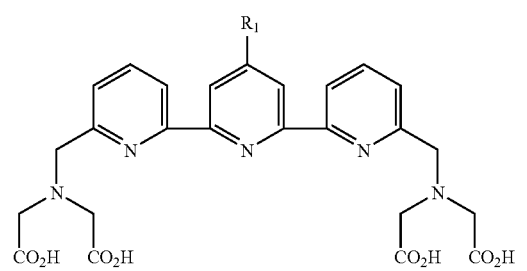

wherein $R_1$ represents a 4-biphenyl group or a 4-biphenyl group having an active substituent or a compound represented by the general formula [2]:

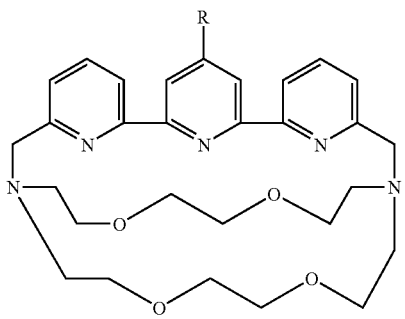

wherein R represents an aryl group, an aryl group having an active substituent, a heterocyclic group or a heterocyclic group having an active substituent
and has a binding group capable of binding to a substance to be labeled and a binding group capable of forming a complex together with a rare earth ion.

2. The labeling reagent according to claim 1, wherein wherein $R_1$ is a 4'-amino-4-biphenyl group.

3. The labeling reagent according to claim 1, wherein R in formula [2] is a 4-biphenyl group.

4. A complex comprising the labeling reagent according to claim 1 and a rare earth metal ion.

5. A fluorescent labeling agent comprising a complex comprising the labeling reagent according to claim 1 and a rare earth metal ion.

6. The fluorescent labeling agent according to claim 5, wherein the rare earth metal ion is a trivalent europium ion, a trivalent samarium ion, a trivalent terbium ion or a trivalent dysprosium ion.

7. A fluorescent labeling method comprising:
utilizing, as a labeling agent, a complex comprising the labeling reagent according to claim 1, and a rare earth metal ion.

8. A fluorescent labeling method comprising:
utilizing the labeling reagent as claimed in claim 1, and a rare earth metal ion.

9. A biological substance or a physiologically active substance labeled with a fluorescent labeling agent comprising a complex comprising the labeling reagent according to claim 1 and a rare earth metal ion.

10. A biological substance or a physiologically active substance being fluorescently labeled by using the labeling reagent according to claim 1 and a rare earth metal ion.

11. The labeled biological substance or physiologically active substance according to claim 9, wherein the biological substance or the physiologically active substance is an enzyme, a protein, a hormone, a peptide, a nucleic acid, a nucleic acid probe, an oligonucleotide, a medicinal substance or an antibiotic.

12. A fluorescence assay method comprising utilizing, as a fluorescent labeling agent, a complex comprising the labeling reagent according to claim 1, and a rare earth metal ion.

13. A fluorescence assay method comprising utilizing the labeling reagent according to claim 1, and a rare earth metal ion.

14. The fluorescence assay method according to claim 12, wherein the fluorescence assay method is a time-resolved fluorescence assay method.

15. The fluorescence assay method according to claim 14, wherein the time-resolved fluorescence assay method is a time-resolved fluoroimmunoassay, a time-resolved fluorescence DNA hybridization assay, a time-resolved fluorescence microscopic imaging or a time-resolved fluorescence chromatography.

16. A reagent for a fluorescence assay method comprising, as a fluorescent labeling agent, a complex comprising the labeling reagent according to claim 1, and a rare earth metal ion.

17. The reagent for a fluorescence assay method comprising the labeling reagent according to claim 1, and a rare earth metal ion.

18. The reagent for a fluorescence assay method according to claim 16, wherein a biological substance or a physiologically active substance is measured.

19. The reagent for a fluorescence assay method according to claim 18, wherein the biological substance or a physiologically active substance is an enzyme, a protein, a hormone, a peptide, a nucleic acid, a nucleic acid probe, an oligonucleotide, a medicinal substance or an antibiotic.

20. A reagent kit comprising, as a fluorescent labeling agent, a complex comprising the labeling reagent according to claim 1 and a rare earth metal ion.

21. A reagent kit comprising the labeling reagent according to claim 1 and a rare earth metal ion.

22. A compound represented by the general formula [1]:

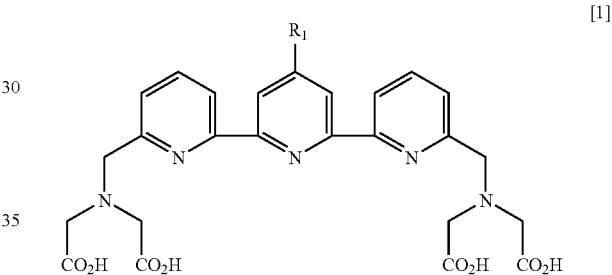

or a salt thereof,
wherein $R_1$ represents a 4-biphenyl group or a 4-biphenyl group having an active substituent.

23. The compound according to claim 22, wherein the compound is represented by the general formula [1-1]:

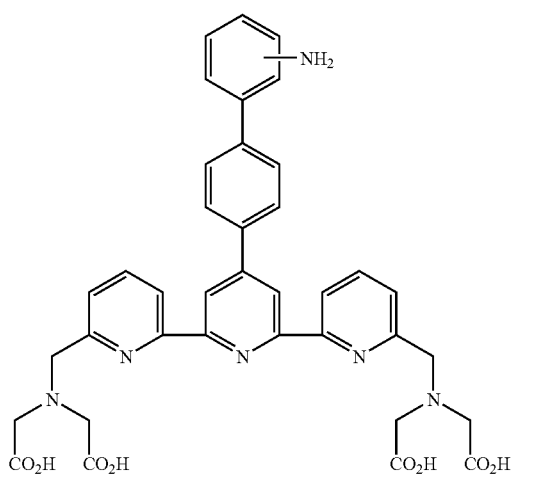

or a salt thereof.

24. A compound represented by the general formula [2]:

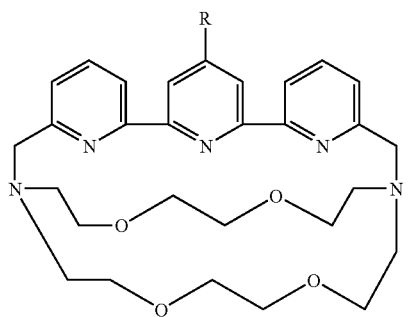

or a salt thereof,
wherein R represents an aryl group, an aryl group having an active substituent, a heterocyclic group or a heterocyclic group having an active substituent.

25. The compound according to claim 24, wherein the compound is represented by the general formula [2-1]:

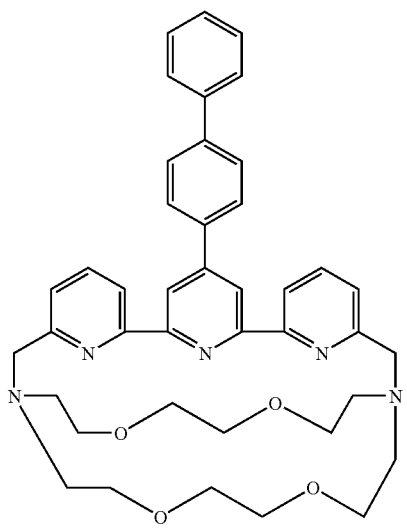

or a salt thereof.

26. The fluorescence assay method according to claim 13, wherein the fluorescence assay method is a time-resolved fluorescence assay method.

27. The fluorescence assay method according to claim 26, wherein the time-resolved fluorescence assay method is a time-resolved fluoroimmunoassay, a time-resolved fluorescence DNA hybridization assay, a time-resolved fluorescence microscopic imaging or a time-resolved fluorescence chromatography.

28. The reagent for a fluorescence assay method according to claim 17, wherein a biological substance or a physiologically active substance is measured.

29. The reagent for a fluorescence assay method according to claim 28, wherein the biological substance or a physiologically active substance is an enzyme, a protein, a hormone, a peptide, a nucleic acid, a nucleic acid probe, an oligonucleotide, a medicinal substance or an antibiotic.

* * * * *